(12) United States Patent
Seya et al.

(10) Patent No.: US 9,090,650 B2
(45) Date of Patent: Jul. 28, 2015

(54) NUCLEIC ACID HAVING ADJUVANTICITY AND USE THEREOF

(75) Inventors: Tsukasa Seya, Sapporo (JP); Misako Matsumoto, Sapporo (JP)

(73) Assignee: National University Corporation Hokkaido University, Sapporo-shi, Hokkaido (JP)

( * ) Notice: Subject to any disclaimer, the term of this patent is extended or adjusted under 35 U.S.C. 154(b) by 159 days.

(21) Appl. No.: 13/812,442

(22) PCT Filed: Jul. 27, 2011

(86) PCT No.: PCT/JP2011/067143
§ 371 (c)(1),
(2), (4) Date: Mar. 6, 2013

(87) PCT Pub. No.: WO2012/014945
PCT Pub. Date: Feb. 2, 2012

(65) Prior Publication Data
US 2013/0178611 A1    Jul. 11, 2013

(30) Foreign Application Priority Data

Jul. 28, 2010    (JP) .................. 2010-169407

(51) Int. Cl.
| | | |
|---|---|---|
| C07H 21/04 | (2006.01) | |
| C07H 21/02 | (2006.01) | |
| A61K 39/00 | (2006.01) | |
| A61K 39/39 | (2006.01) | |
| A61K 31/711 | (2006.01) | |
| A61K 31/713 | (2006.01) | |
| C12N 15/117 | (2010.01) | |

(52) U.S. Cl.
CPC .............. *C07H 21/04* (2013.01); *A61K 31/711* (2013.01); *A61K 31/713* (2013.01); *A61K 39/0011* (2013.01); *A61K 39/39* (2013.01); *C07H 21/02* (2013.01); *C12N 15/117* (2013.01); *A61K 2039/55561* (2013.01); *A61K 2039/58* (2013.01)

(58) Field of Classification Search
None
See application file for complete search history.

(56) References Cited

U.S. PATENT DOCUMENTS

2003/0232074 A1* 12/2003 Lipford et al. ................ 424/450
2008/0311112 A1* 12/2008 Hackam et al. ............ 424/130.1

FOREIGN PATENT DOCUMENTS

| WO | WO-2006054117 A2 | 5/2006 |
|---|---|---|
| WO | WO-2006125977 A2 | 11/2006 |
| WO | WO-2007122392 A1 | 11/2007 |
| WO | WO-2008/065752 A1 | 6/2008 |
| WO | WO-2009088401 A2 | 7/2009 |

OTHER PUBLICATIONS

Sugiyama et al (International Immunology, vol. 20, No. 1, pp. 1-9).*
Extended European Search Report in EP 11 81 2534 dated Jul. 7, 2014.
Ghosh et al., "TLR-TLR cross talk in human PBMC resulting in synergistic and antagonistic regulation of type-1 and 2 interferons, IL-12 and TNF-α," *International Immunopharmacology*, vol. 7, pp. 1111-1121 (2007).
Bagchi et al., "MyD88-Dependent and MyD88-Independent Pathways in Synergy, Priming, and Tolerance between TLR Agonists," *The Journal of Immunology*, vol. 178, No. 2, pp. 1164-1171 (2007).
Napolitani et al., Selected Toll-like receptor agonist combinations synergistically trigger a T helper type 1-polarizing program in dendritic cells, *Nature Immunology*, vol. 6, No. 8, pp. 769-776 (2005).
Ranjith-Kumar et al, "Single-Stranded Oligonucleotides Can Inhibit Cytokine Production Induced by Human Toll-Like Receptor 3," *Molecular and Cellular Biology*, vol. 28, No. 14, pp. 4507-4519 (2008).
Zheng et al., "Paired Toll-like Receptor Agonists Enhance Vaccine Therapy through Induction of Interleukin-12," *Cancer Research*, vol. 68, No. 11, pp. 4045-4049 (2008).
Zhu et al., "Toll-like receptor ligands synergize through distinct dendritic cell pathways to induce T cell responses: Implications for vaccines," *Proceedings of the National Academy of Sciences*, vol. 105, No. 42, pp. 16260-16265 (2008).
Itoh et al., "The Clathrin-Mediated Endocytic Pathway Participates in dsRNA-Induced IFN-β Production," *The Journal of Immunology* 81(8), 5522-5529 (2008).
International Search Report in corresponding PCT/JP2011/067143 mailed Oct. 11, 2011.
Written Opinion of the ISA in corresponding PCT/JP2011/067143 mailed Oct. 11, 2011.
International Preliminary Report on Patentability in corresponding PCT/JP2011/067143 mailed Jun. 1, 2012.
Jin et al., "Immunomodulatory Effects of dsRNA and Its Potential as Vaccine Adjuvant", *Journal of Biomedicine and Biotechnology*, vol. 2010, pp. 1-17 (2010).
Lau et al., "A TLR3 ligand that exhibits potent inhibition of influenza virus replication and has strong adjuvant activity has the potential for dual applications in an influenza pandemic", *Vaccine* 27, pp. 1354-1364 (2009).

* cited by examiner

*Primary Examiner* — Richard Schnizer

(57) ABSTRACT

The disclosed nucleic acid at least containing a single-stranded DNA to be delivered to endosomes of dendritic cells and a double-stranded RNA capable of activating TLR3 can be delivered to endosomal TLR3 and has a strong adjuvanticity with few side effects, and therefore is useful as an active ingredient of immunostimulants, vaccine adjuvants, cancer therapeutic agents and the like.

14 Claims, 20 Drawing Sheets

Fig. 6-A
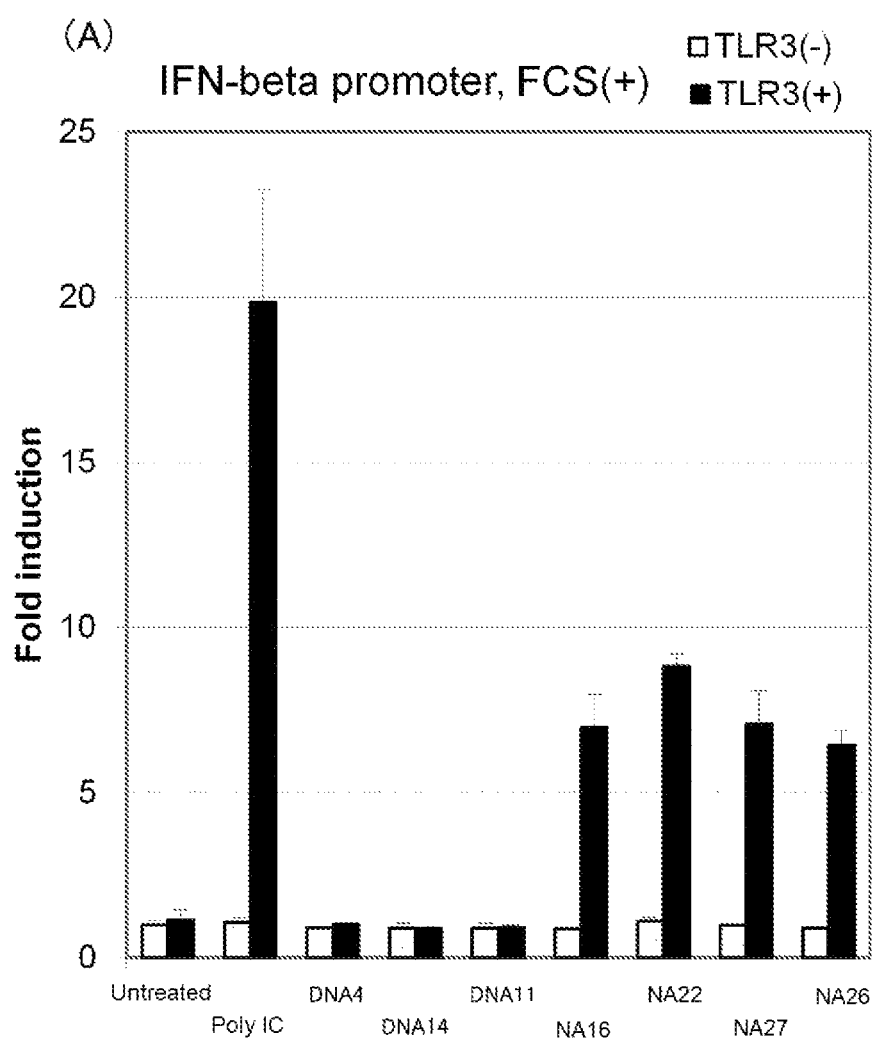

Fig. 6-B
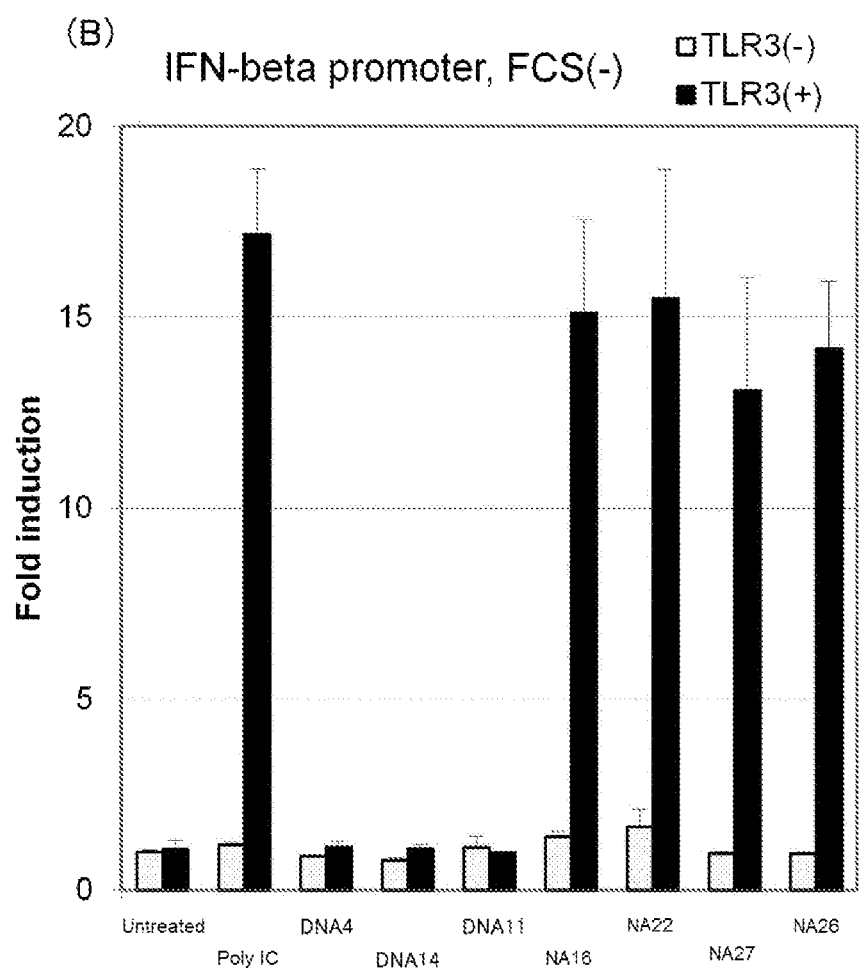

Fig. 8-A
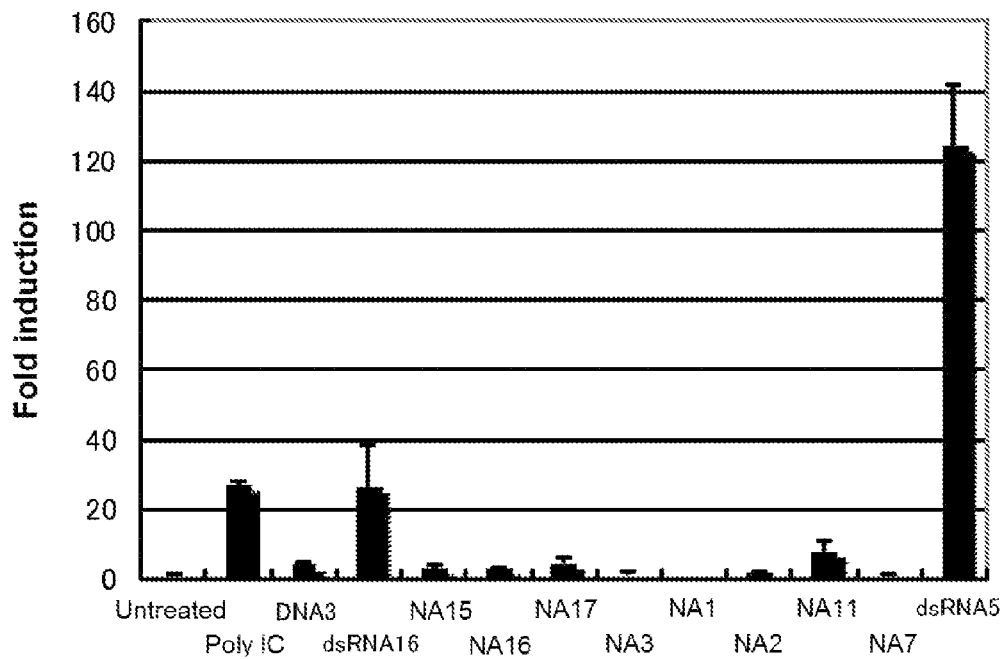

Fig. 8-B
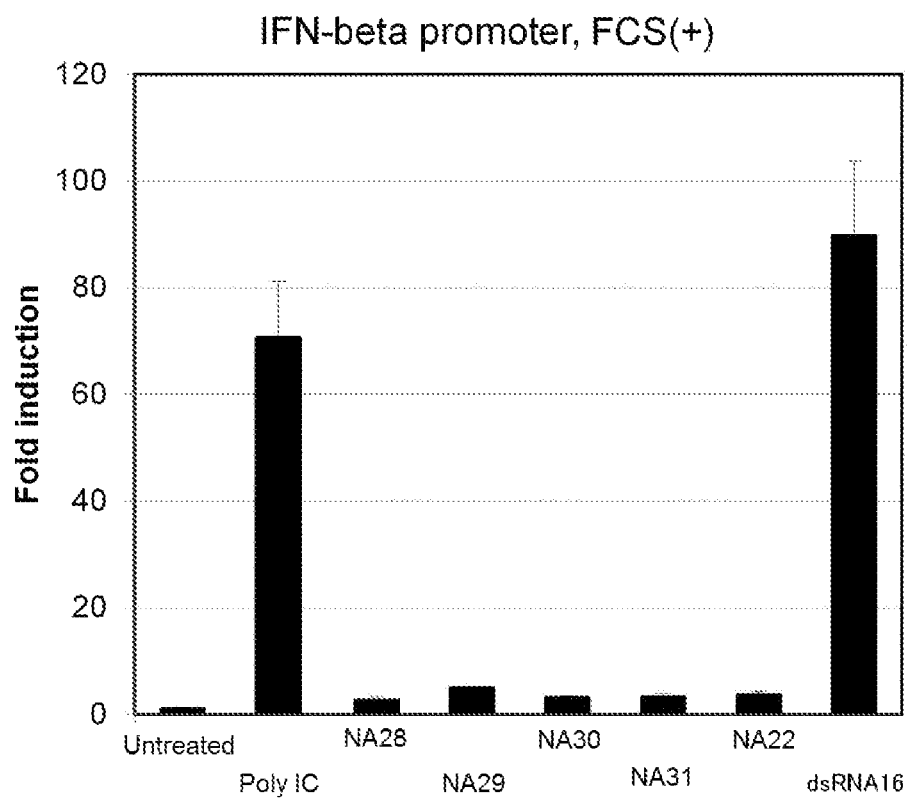

Fig. 9-A
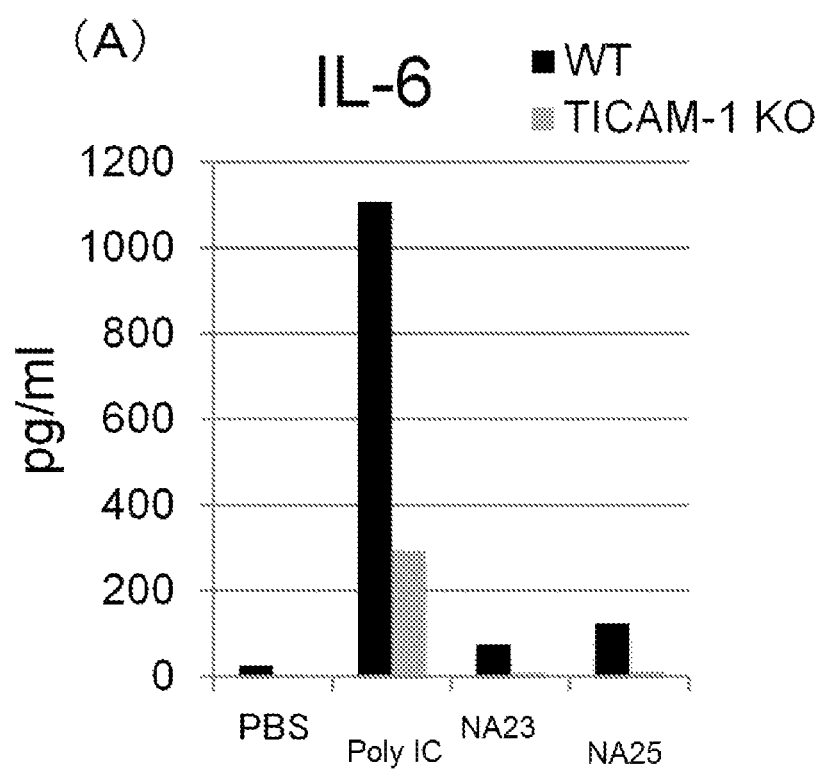

Fig. 9-B
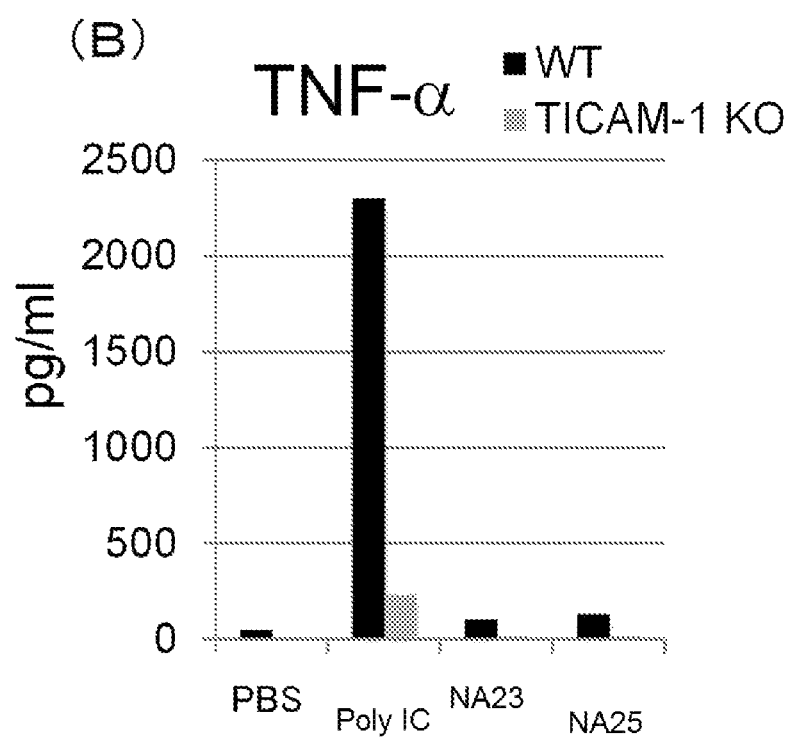

Fig. 9-C
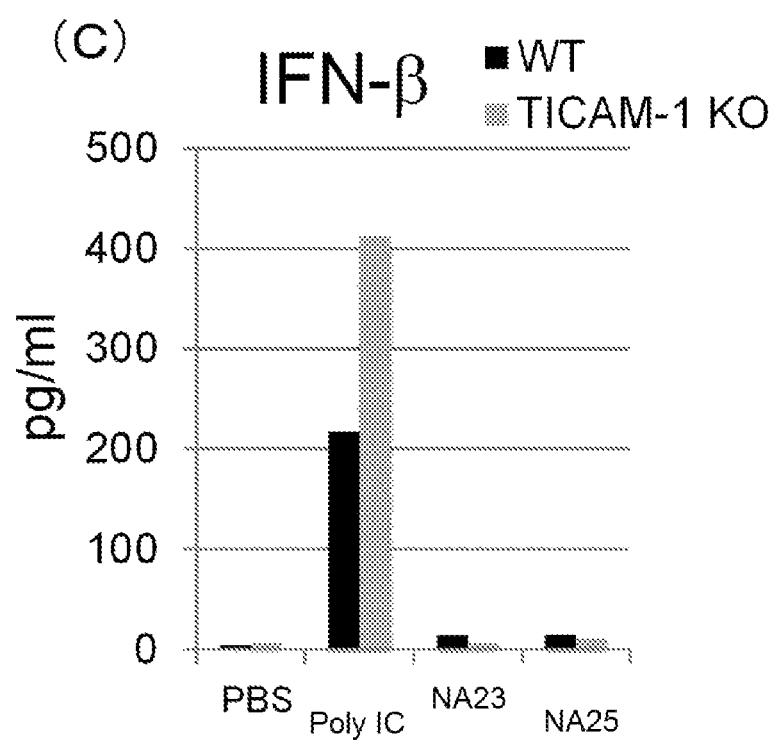

Fig. 10-A
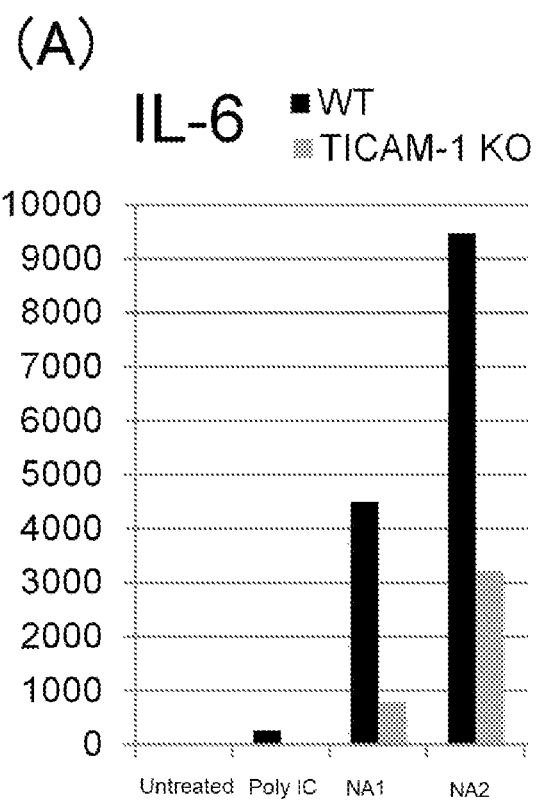

Fig. 10-B
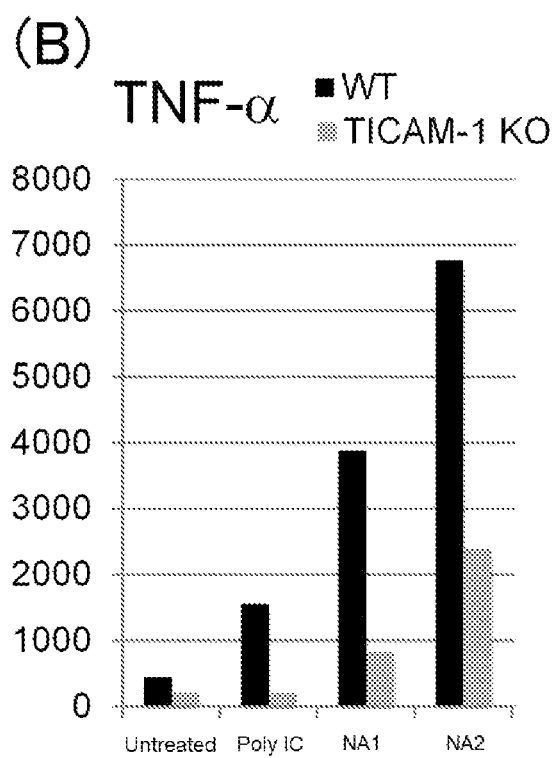

Fig. 11-A
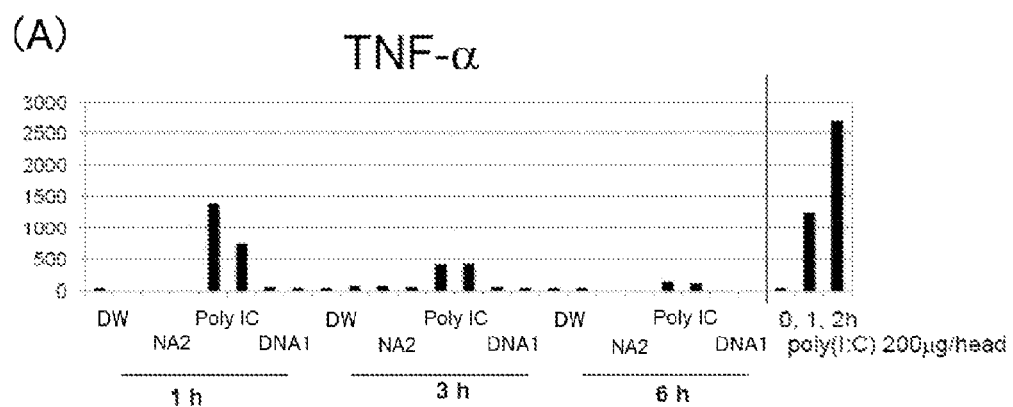
Fig. 11-B
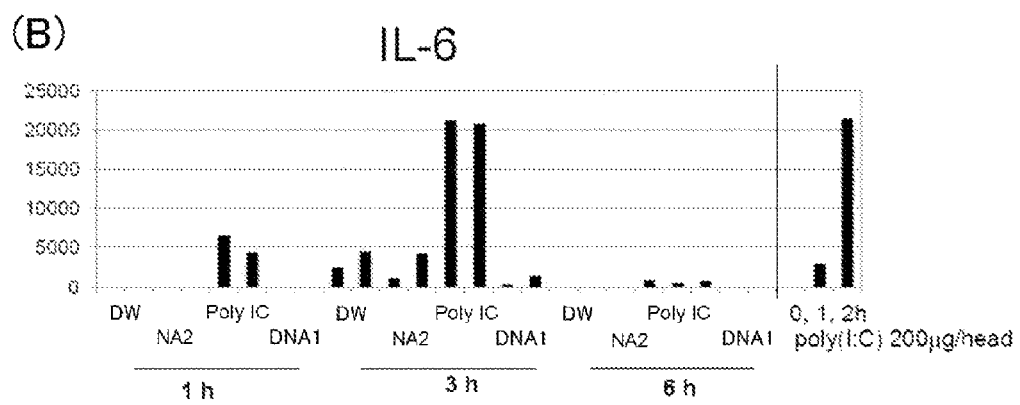

Fig. 11-C
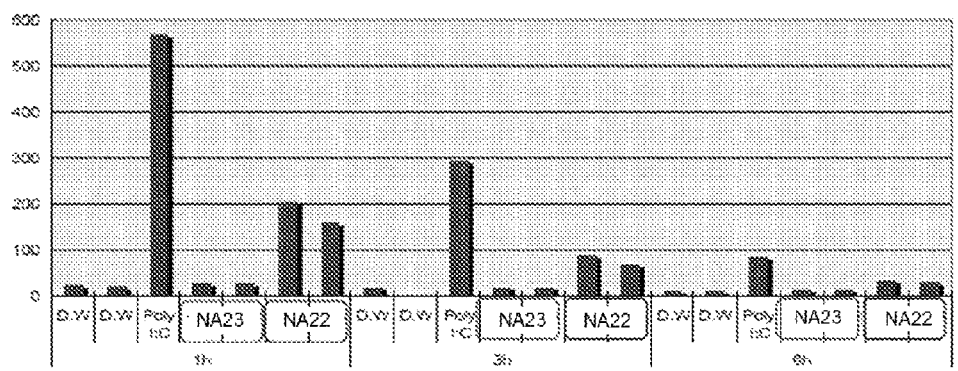
Fig. 11-D
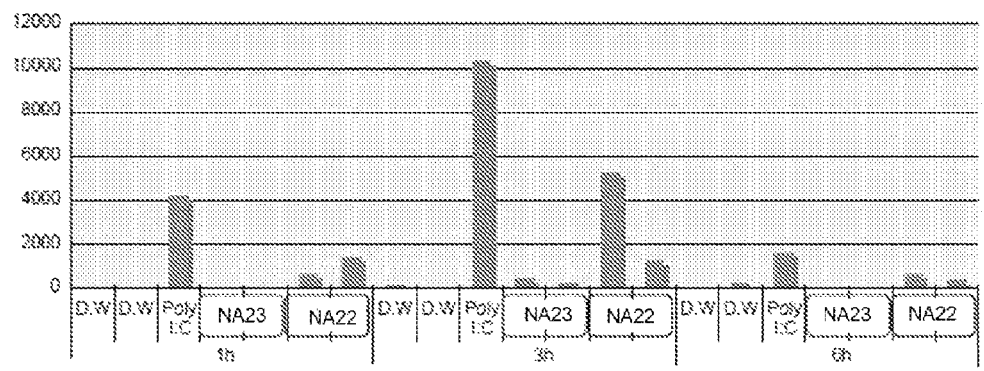

Fig. 11-E
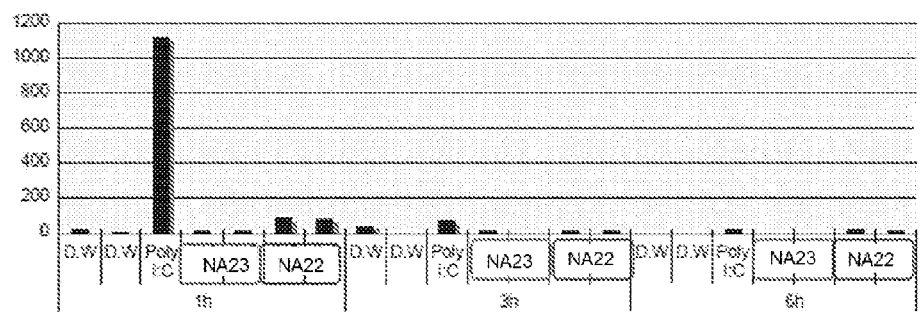
Fig. 12
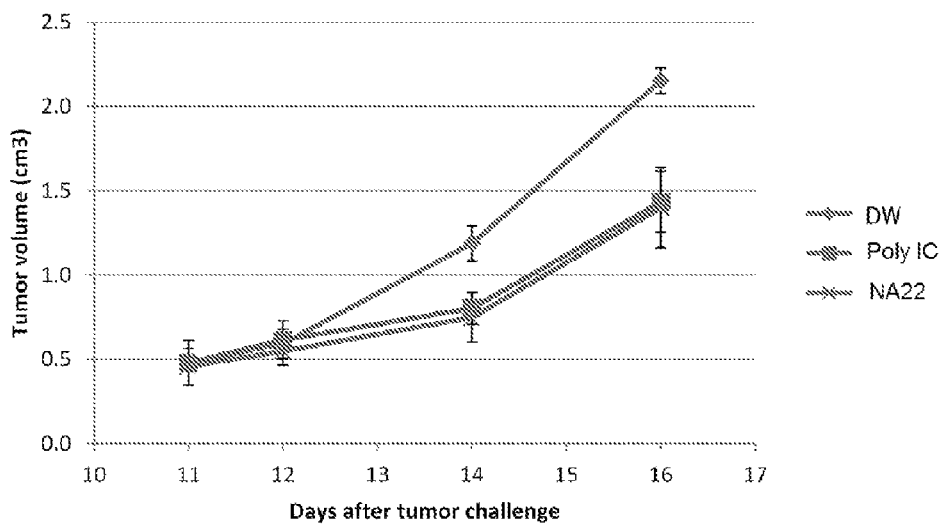

Fig. 13
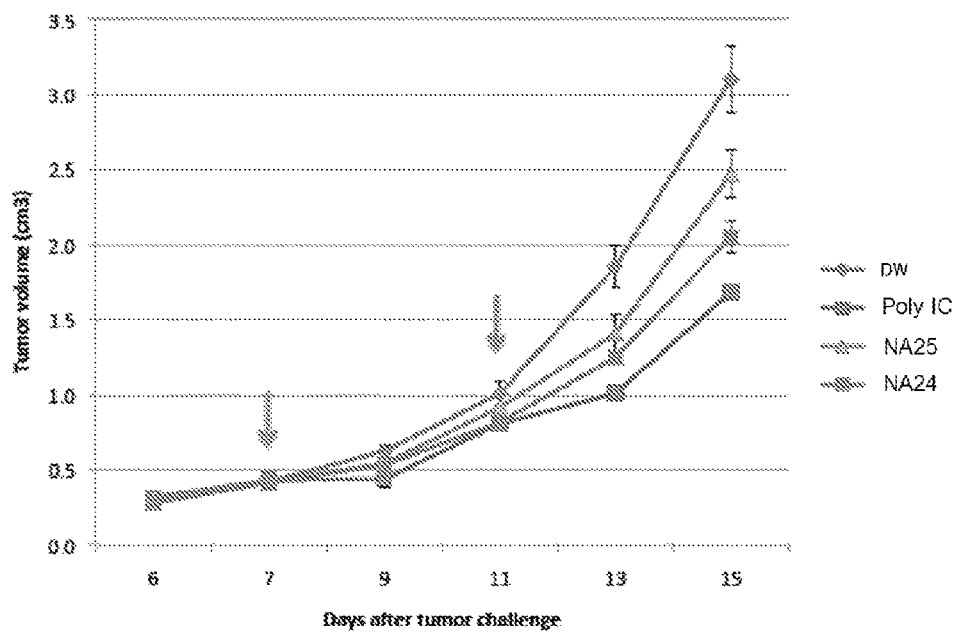
Fig. 14-A
(A)
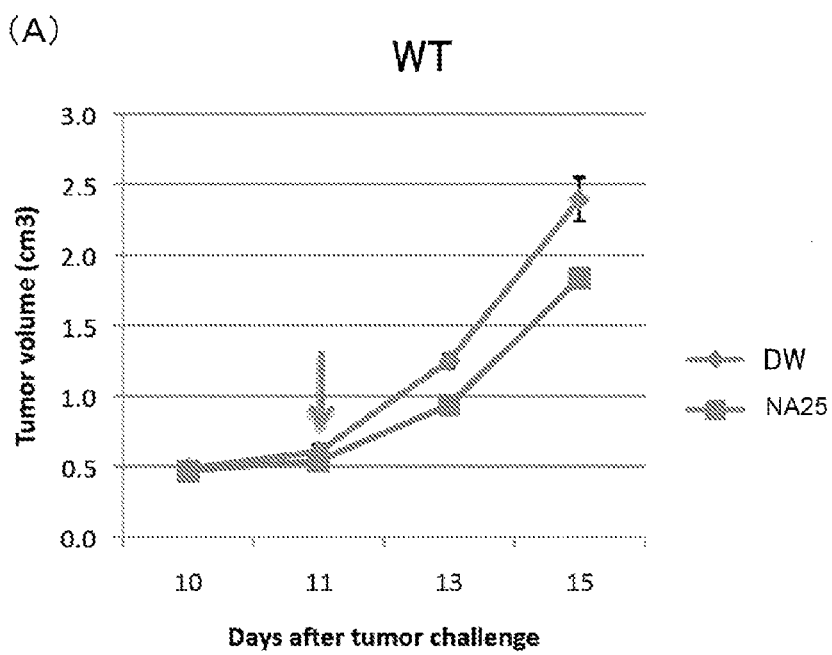

Fig. 14-B

NUCLEIC ACID HAVING ADJUVANTICITY AND USE THEREOF

TECHNICAL FIELD

The present invention relates to a novel nucleic acid having adjuvanticity; and a pharmaceutical composition, an IFN-β expression enhancer, an NK cell activator, a cytotoxic T cell inducer, an immunostimulant, a vaccine adjuvant and a cancer therapeutic agent each containing the nucleic acid.

BACKGROUND ART

As a method for cancer treatment, there is so-called cancer immunotherapy that enhances patient's own immunity against cancer cells to induce cancer regression. The main procedure of this cancer immunotherapy is administration of a peptide vaccine as a cancer antigen. For increased efficacy, simultaneous administration of a cancer antigen together with an adjuvant which activates dendritic cells has been proposed.

The present inventors have advanced the research on adjuvants used for cancer immunotherapy, and to date, they have found that measles viral diRNA (defective interference RNA) functions as an adjuvant and disclosed this finding in Patent Literature 1. Specifically, it is disclosed that the diRNA induces IFN-β expression in human cells and enhances the NK activity of NK cells, and that the diRNA administered with a cancer antigen epitope to cancer-bearing mice which had been established by inoculation of B16 melanoma cells, shows a marked effect on cancer regression. However, the problem has arisen that the diRNA exhibits an insufficient adjuvanticity when extracellularly administered because the extracellularly administered diRNA cannot be delivered to endosomal TLR3 (Toll-like receptor 3). Meanwhile, poly IC, which is widely known as a synthetic TLR3 ligand, exhibits a strong adjuvanticity in extracellular administration but may cause side effects, such as overproduction of cytokines (cytokine storm), and thus unfortunately cannot be applied in a clinical setting.

Aside from this, the present inventors have identified an oligo DNA that inhibits poly IC-inducible IFN-β expression mediated by TLR3, and reported that the oligo DNAs are internalized into cells via the same receptor as that for poly IC and partly colocalized with TLR3 (Non Patent Literature 1). However, Non Patent Literature 1 does not suggest that the oligo DNA is capable of delivering another nucleic acid linked thereto to endosomal TLR3, and it would have been unpredictable whether the oligo DNA described in Non Patent Literature 1 can deliver the stem-loop structured diRNA described in Patent Literature 1 to endosomal TLR3 by linking to the diRNA.

CITATION LIST

Patent Literature

Patent Literature 1:
WO 2008/065752

Non Patent Literature

Non Patent Literature 1:
The Journal of Immunology, 2008, 181: 5522-5529

SUMMARY OF INVENTION

Technical Problem

An object of the present invention is to provide a nucleic acid which can be delivered to endosomal TLR3 and has a strong adjuvanticity with few side effects.

Solution to Problem

The present invention includes the following as a solution to the above-mentioned problems.
(1) A nucleic acid at least containing a single-stranded DNA to be delivered to endosomes of dendritic cells and a double-stranded RNA capable of activating TLR3.
(2) The nucleic acid according to the above (1), wherein the single-stranded DNA is any of the following (a) to (d):
(a) a type-B or -C CpG-DNA having TLR9 ligand activity,
(b) a DNA which is the same as the above (a) except for having GpC instead of CpG,
(c) a DNA which is the same as the above (b) except for having TpC instead of GpC, and
(d) a DNA which is the same as the above (b) except for having CpC instead of GpC.
(3) The nucleic acid according to the above (2), wherein the single-stranded DNA consists of a base sequence shown in any of SEQ ID NOS: 1 to 4 and 11 to 14, or of a partial sequence thereof.
(4) The nucleic acid according to any of the above (1) to (3), wherein the single-stranded DNA has 15 bases or more in length.
(5) The nucleic acid according to any of the above (1) to (4), wherein all or part of nucleotides which constitute the single-stranded DNA are phosphorothioated.
(6) The nucleic acid according to any of the above (1) to (5), wherein the double-stranded RNA capable of activating TLR3 has an RNA virus-derived RNA sequence.
(7) The nucleic acid according to the above (6), wherein the RNA virus is selected from a measles virus, a sendai virus, an RS virus, a hepatitis C virus, a poliovirus and a rotavirus.
(8) The nucleic acid according to the above (7), wherein the double-stranded RNA capable of activating TLR3 is an RNA consisting of a base sequence shown in any of SEQ ID NOS: 5 to 7 and 15 to 20 and of a complementary sequence thereof.
(9) The nucleic acid according to any of the above (1) to (8), wherein the double-stranded RNA capable of activating TLR3 has 40 to 200 base pairs in length.
(10) The nucleic acid according to any of the above (1) to (9), wherein the single-stranded DNA is linked to the double-stranded RNA via a linker sequence.
(11) The nucleic acid according to any of the above (1) to (9), wherein the single-stranded DNA is directly linked to the double-stranded RNA.
(12) A pharmaceutical composition containing the nucleic acid according to any of the above (1) to (11).
(13) An IFN-β expression enhancer containing the nucleic acid according to any of the above (1) to (11) as an active ingredient.
(14) An NK cell activator containing the nucleic acid according to any of the above (1) to (11) as an active ingredient.
(15) A cytotoxic T cell inducer containing the nucleic acid according to any of the above (1) to (11) as an active ingredient.
(16) An immunostimulant containing the nucleic acid according to any of the above (1) to (11) as an active ingredient.

(17) A vaccine adjuvant containing the nucleic acid according to any of the above (1) to (11) as an active ingredient.
(18) A cancer therapeutic agent containing the nucleic acid according to any of the above (1) to (11) as an active ingredient.
(19) A method for cancer treatment, comprising administering an effective amount of the nucleic acid according to any of the above (1) to (11) to a mammal.
(20) Use of the nucleic acid according to any of the above (1) to (11) for production of a cancer therapeutic agent.
(21) A nucleic acid according to any of the above (1) to (11) for use for cancer treatment.

Advantageous Effects of Invention

The present invention can provide a nucleic acid which can be delivered to endosomal TLR3 and has a strong adjuvanticity with few side effects. The nucleic acid of the present invention can enhance IFN-β expression, activate NK cells and induce cytotoxic T cells, and therefore is highly useful as an immunostimulant and a vaccine adjuvant. Further, the nucleic acid exhibits a strong tumor-regression effect when administered alone, and therefore is useful as a cancer therapeutic agent.

BRIEF DESCRIPTION OF DRAWINGS

FIG. 6(A) shows the results of the effect that the base sequence of the endosomal localization sequence (ssDNA) in the nucleic acid of the present invention makes on IFN-β promoter activation in a culture medium with FCS.

FIG. 6(B) shows the results of the effect that the base sequence of the endosomal localization sequence (ssDNA) in the nucleic acid of the present invention makes on IFN-β promoter activation in a culture medium without FCS.

FIG. 8(A) shows the results of RIG-I/MDA5-mediated IFN-β promoter activation by nucleic acids of the present invention in a culture medium with FCS.

FIG. 8(B) shows the results of RIG-I/MDA5-mediated IFN-β promoter activation by nucleic acids of the present invention in a culture medium with FCS.

FIG. 9(A) shows the results of in vitro IL-6 production by nucleic acids of the present invention in wild-type or TICAM-1 KO mouse splenic dendritic cells.

FIG. 9(B) shows the results of in vitro TNF-α production by nucleic acids of the present invention in wild-type or TICAM-1 KO mouse splenic dendritic cells.

FIG. 9(C) shows the results of in vitro IFN-β production by nucleic acids of the present invention in wild-type or TICAM-1 KO mouse splenic dendritic cells.

FIG. 10(A) shows the results of in vitro IL-6 production by nucleic acids of the present invention in wild-type or TICAM-1 KO mouse bone marrow dendritic cells.

FIG. 10(B) shows the results of in vitro TNF-α production by nucleic acids of the present invention in wild-type or TICAM-1 KO mouse bone marrow dendritic cells.

FIG. 11(A) shows the results of TNF-α production by NA2 in evaluation of in vivo cytokine production by nucleic acids of the present invention.

FIG. 11(B) shows the results of IL-6 production by NA2 in evaluation of in vivo cytokine production by nucleic acids of the present invention.

FIG. 11(C) shows the results of TNF-α production by NA22 and NA23 in evaluation of in vivo cytokine production by nucleic acids of the present invention.

FIG. 11(D) shows the results of IL-6 production by NA22 and NA23 in evaluation of in vivo cytokine production by nucleic acids of the present invention.

FIG. 11(E) shows the results of IL-10 production by NA22 and NA23 in evaluation of in vivo cytokine production by nucleic acids of the present invention.

FIG. 12 shows the results of the effect on regression of transplanted cancer by a nucleic acid of the present invention in B16 melanoma-bearing wild-type mice.

FIG. 13 shows the results of the effect on regression of transplanted cancer by nucleic acids of the present invention in EL4-bearing wild-type mice.

DESCRIPTION OF EMBODIMENTS

<Nucleic Acid of Present Invention>

Figure 1:
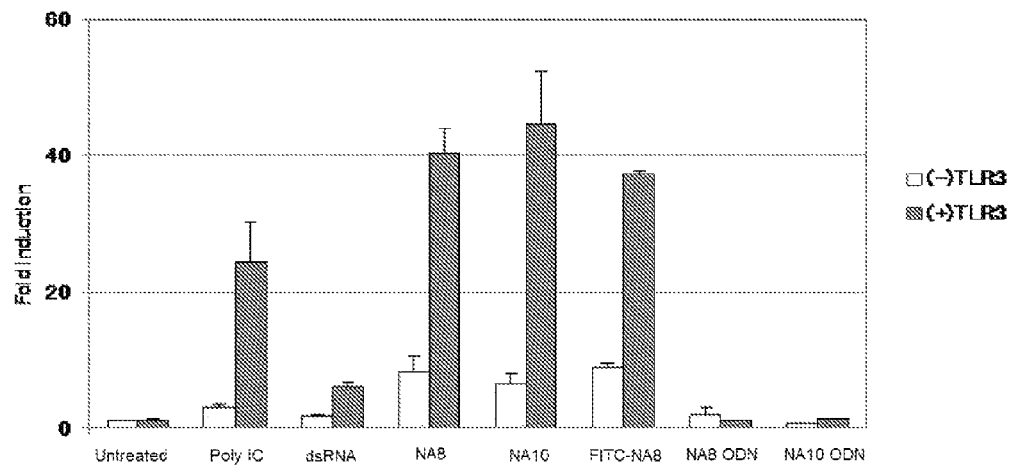
FIG. 1 shows the results of IFN-β promoter activation by nucleic acids of the present invention in a culture medium without FCS.

The nucleic acid of the present invention may be any nucleic acid that at least contains a single-stranded DNA (ssDNA) to be delivered to endosomes of dendritic cells and a double-stranded RNA (dsRNA) capable of activating TLR3.

The ssDNA to be delivered to endosomes of dendritic cells is not particularly limited as long as the ssDNA can be internalized into dendritic cells from extracellular environment and then delivered to endosomes. As the ssDNA, preferred is any of the following (a) to (d):
(a) a type-B or -C CpG-DNA having TLR9 ligand activity,
(b) a DNA which is the same as the above (a) except for having GpC instead of CpG, (c) a DNA which is the same as the above (b) except for having TpC instead of GpC, and
(d) a DNA which is the same as the above (b) except for having CpC instead of GpC.

CpG-DNA is a DNA having a CpG motif characteristic to viral and bacterial genes. Type-B CpG-DNAs strongly induce B cell responses, and type-C TLR9 ligands have actions of both type-B and -A counterparts (strongly inducing responses by NK cells and plasmacytoid dendritic cells). Examples of the ssDNA corresponding to the above (a) include ODN 2006, ODN M362, ODN 2395, ODN 1668, ODN 1826 and ODN 2007 (these are all trade names and manufactured by InvivoGen). The present inventors have confirmed that the DNA which is the same as the above (a) except for having GpC instead of CpG can also be delivered to endosomes of dendritic cells. Further, the present inventors have confirmed that the DNA which is the same as the above (b) except for having TpC or CpC instead of GpC can also be delivered to endosomes of dendritic cells.

Preferable examples of the ssDNA to be delivered to endosomes of dendritic cells include an ssDNA consisting of a base sequence which is shown in any of SEQ ID NOS: 1 to 4 and described in Table 1.

TABLE 1

| Trade name* | Base sequence | SEQ ID |
|---|---|---|
| ODN M362 | tcgtcgtcgttcgaacgacgttgat | 1 |
| ODN M362 control | tgctgctgcttgcaagcagcttgat | 2 |
| ODN 2006 | tcgtcgttttgtcgttttgtcgtt | 3 |
| ODN 2006 control | tgctgcttttgtgcttttgtgctt | 4 |

*manufactured by InvivoGen

In addition, a DNA which is the same as that of SEQ ID NO: 2 except for having TpC instead of GpC (SEQ ID NO: 11), a DNA which is the same as that of SEQ ID NO: 2 except for having CpC instead of GpC (SEQ ID NO: 12), a DNA which is the same as that of SEQ ID NO: 4 except for having TpC instead of GpC (SEQ ID NO: 13), a DNA which is the same as that of SEQ ID NO: 4 except for having CpC instead of GpC (SEQ ID NO: 14), and the like can be preferably used as the ssDNA to be delivered to endosomes of dendritic cells.

The length of the ssDNA to be delivered to endosomes of dendritic cells is not particularly limited, but 5 bases or more has been proven to a sufficient length to produce the desired effects. The preferable length is about 15 bases or more. The maximum limit is not particularly limited, either, but about 25 bases is considered to be a sufficient length to produce the desired effects. Therefore, the length of the ssDNA to be delivered to endosomes of dendritic cells is preferably about 5 to 30 bases and more preferably about 15 to 25 bases. For example, an ssDNA which consists of part (partial sequence) of a base sequence shown in any of SEQ ID NOS: 1 to 4 and 11 to 14 and has 5 bases or more, preferably 15 bases or more in length, can be preferably used.

It is preferable that the ssDNA to be delivered to endosomes of dendritic cells is phosphorothioated (also called "S-modified"). The ssDNA may be partially or fully phosphorothioated, but it is more preferable that the ssDNA is fully phosphorothioated. Phosphorothioation provides DNA with nuclease resistance and improves DNA delivery to endosomes.

The dsRNA capable of activating TLR3 is not limited as long as the dsRNA has the capability of activating TLR3, but it is preferable that the dsRNA has an RNA virus-derived RNA sequence. The RNA virus is not particularly limited and may be any of a negative-sense, single-stranded RNA virus, a positive-sense, single-stranded RNA virus and a double-stranded RNA virus. Specific examples of the RNA virus include a measles virus, a sendai virus, an RS virus, a hepatitis C virus, a poliovirus and a rotavirus. Preferred is a measles virus, a sendai virus or an RS virus, each of which is a negative-sense, single-stranded RNA virus, and more preferred is a vaccine strain of a measles virus, a sendai virus or an RS virus.

The length of the dsRNA capable of activating TLR3 is not particularly limited, but is preferably about 40 base pairs (bps) or more, more preferably about 60 bps or more, and still more preferably about 90 bps. The maximum limit is not particularly limited, either, but about 150 bps is considered to be a sufficient length to produce the desired effects. Therefore, the length of the dsRNA capable of activating TLR3 is preferably about 40 to 200 bps, more preferably about 60 to 180 bps and still more preferably about 90 to 150 bps.

Preferable examples of the dsRNA capable of activating TLR3 include a dsRNA consisting of a base sequence shown in any of SEQ ID NOS: 5 to 7 and 15 to 20 and of its complementary sequence. The base sequence shown in any of SEQ ID NOS: 5 to 7 and 15 to 20 has part of the base sequence (SEQ ID NO: 8) of diRNA derived from an attenuated strain of measles virus, an Edmonston (ED) strain. The base sequence shown in SEQ ID NO: 5 corresponds to positions 1017 to 1074 of SEQ ID NO: 8. The base sequence shown in SEQ ID NO: 6 consists of a base sequence corresponding to positions 1077 to 1152 of SEQ ID NO: 8 and of three additional cytosines at the 5' end. The base sequence shown in SEQ ID NO: 7 consists of a base sequence corresponding to positions 1017 to 1152 of SEQ ID NO: 8 and of three additional cytosines at the 5' end. The base sequence shown in SEQ ID NO: 15 consists of a base sequence corresponding to positions 1077 to 1152 of SEQ ID NO: 8 and of three additional cytosines at the 3' end. The base sequence shown in SEQ ID NO: 16 consists of a base sequence corresponding to positions 1017 to 1152 of SEQ ID NO: 8 and of three additional cytosines at the 3' end. The base sequence shown in SEQ ID NO: 17 consists of a base sequence corresponding to positions 1057 to 1152 of SEQ ID NO: 8 and of three additional cytosines at the 3' end. The base sequence shown in SEQ ID NO: 18 consists of abase sequence corresponding to positions 1046 to 1152 of SEQ ID NO: 8 and of three additional cytosines at the 3' end. The base sequence shown in SEQ ID NO: 19 consists of a base sequence corresponding to positions 1037 to 1152 of SEQ ID NO: 8 and of three additional cytosines at the 3' end. The base sequence shown in SEQ ID NO: 20 corresponds to positions 1017 to 1089 of SEQ ID NO: 8.

The nucleic acid of the present invention may consist of an ssDNA to be delivered to endosomes of dendritic cells and of a dsRNA capable of activating TLR3, or consist of the ssDNA, the dsRNA and another nucleic acid (hereinafter called "additional nucleic acid"). The ssDNA may be linked to either strand of the dsRNA. The ssDNA may be directly linked to the dsRNA or linked thereto via the additional nucleic acid. The ssDNA-dsRNA link may be located either between the 3' end of the ssDNA and the 5' end of the dsRNA, or between the 5' end of the ssDNA and the 3' end of the dsRNA, but the former is preferred.

In the case where the nucleic acid of the present invention consists of an ssDNA to be delivered to endosomes of dendritic cells, a dsRNA capable of activating TLR3, and another nucleic acid (hereinafter called "additional nucleic acid"), the additional nucleic acid may be a single- or double-stranded DNA, a single- or double-stranded RNA, or a DNA-RNA hybrid. Preferred is a double-stranded RNA or a DNA-RNA hybrid. In the case where the ssDNA to be delivered to endosomes of dendritic cells is directly linked to the dsRNA capable of activating TLR3, the additional nucleic acid may be linked to the other end of either the ssDNA or the dsRNA, or to the other ends of both the ssDNA and the dsRNA, but is preferably linked to the 3' end of the ssDNA or the dsRNA. Unless the functions of the nucleic acid of the present invention are hindered, the length (the number of bases) of the additional nucleic acid is not limited.

Alternatively, the ssDNA to be delivered to endosomes of dendritic cells may be linked to the dsRNA capable of activating TLR3 via the additional nucleic acid, that is, a linker sequence. The linker sequence may be a single- or double-stranded DNA, a single- or double-stranded RNA, or a DNA-RNA hybrid. Preferred is a double-stranded RNA or a DNA-RNA hybrid. Unless the functions of the nucleic acid of the present invention are hindered, the length (the number of bases) of the linker sequence is not limited. Yet another nucleic acid may be linked to the other end of either the ssDNA or the dsRNA, or to the other ends of both the ssDNA and the dsRNA. In this case, such a nucleic acid is preferably linked to the 3' end of the dsRNA.

The nucleic acid of the present invention can be produced according to a known method without particular limitation. For example, general chemical synthesis methods of nucleic acids can be preferably used. For production of RNA strands, a known in vitro transcription can be preferably used. Specifically, the nucleic acid of the present invention can be produced by separately synthesizing a strand having DNA and RNA linked to each other, and an RNA complementary strand, and allowing both strands to form a double strand under appropriate conditions. The nucleic acid of the present invention further containing the additional nucleic acid can be produced similarly.

<Use of Nucleic Acid of Present Invention>

Since the nucleic acid of the present invention can be delivered to endosomes of dendritic cells and activate TLR3, the nucleic acid can enhance various immune reactions. Specifically, the nucleic acid can enhance IFN-β expression, activate NK cells, and induce cytotoxic T cells. Therefore, the present invention provides an IFN-β expression enhancer, an NK cell activator, a cytotoxic T cell inducer, an immunostimulant and a vaccine adjuvant each containing the nucleic acid of the present invention as an active ingredient. Further, it has been shown that the nucleic acid of the present invention, when administered alone to mice bearing tumors formed by subcutaneous inoculation of cancer cells, makes the tumors regress and thus is useful for cancer treatment. Therefore, the present invention provides a cancer therapeutic agent containing the nucleic acid of the present invention as an active ingredient.

Each of the above-mentioned medicines containing the nucleic acid of the present invention as an active ingredient is greatly useful due to few side effects. While the synthetic TLR3 ligand poly IC activates not only TLR3 but also an intracellular RNA sensor RIG/MDA5 and thus may induce cytokine storm, the dsRNA capable of activating TLR3 in the nucleic acid of the present invention, unlike poly IC, selectively activates a TICAM-1-mediated signal transduction pathway downstream of TLR3, and thus is least likely to induce cytokine storm.

The pharmaceutical composition of the present invention can be prepared by appropriately blending the nucleic acid of the present invention and a pharmaceutically acceptable carrier or additive, and formulated into a dosage form. Specific examples of the dosage form include oral preparations such as tablets, coated tablets, pills, powders, granules, capsules, solutions, suspensions and emulsions; and parenteral preparations such as injections, infusions, suppositories, ointments and patches. The blending ratio of the carrier or the additive is appropriately determined based on the range of the blending ratio conventionally adopted in the pharmaceutical field. The carrier or the additive that can be blended is not particularly limited, and examples thereof include various carriers such as water, physiological saline, other aqueous solvents and aqueous or oily bases; and various additives such as excipients, binders, pH adjusters, disintegrants, absorption enhancers, lubricants, colorants, corrigents and fragrances.

Examples of the additive that can be blended into tablets, capsules and the like include binders such as gelatin, cornstarch, tragacanth and gum arabic; excipients such as crystalline cellulose; bulking agents such as cornstarch, gelatin and alginic acid; lubricants such as magnesium stearate; sweeteners such as sucrose, lactose and saccharin; and flavors such as peppermint, Gaultheria adenothrix oil and cherry. In the case where the unit dosage form is a capsule, a liquid carrier such as fats and oils can be further blended in addition to the above-mentioned materials. A sterile composition for injection can be prepared according to an ordinary pharmaceutical formulation practice, for example, by dissolving or suspending an active substance in a vehicle such as water for injection and a natural vegetable oil (such as sesame oil and coconut oil). As an aqueous liquid for injection, for example, physiological saline, an isotonic solution containing glucose and an auxiliary substance (for example, D-sorbitol, D-mannitol, sodium chloride, etc.), or the like can be used, optionally together with a suitable solubilizer such as alcohols (for example, ethanol), polyalcohols (for example, propylene glycol, polyethylene glycol) and nonionic surfactants (for example, polysorbate 80™, HCO-50). As an oily liquid, for example, sesame oil, soybean oil or the like can be used, optionally together with a solubilizer such as benzyl benzoate and benzyl alcohol. Further, a buffering agent (for example, a phosphate buffer, a sodium acetate buffer), a soothing agent (for example, benzalkonium chloride, procaine hydrochloride, etc.), a stabilizer (for example, human serum albumin, polyethylene glycol, etc.), a preservative (for example, benzyl alcohol, phenol, etc.), an antioxidant, etc. may also be blended.

The pharmaceutical preparation that can be obtained in the above manner can be administered to, for example, humans and other mammals (rats, mice, rabbits, sheep, pigs, cows, cats, dogs, monkeys, etc.). The pharmaceutical composition of the present invention, when administered as a vaccine adjuvant, should be administered with an antigen which acts as a vaccine.

The dose and dosing frequency of the pharmaceutical composition of the present invention is appropriately determined in consideration of the purpose, the age, body weight, sex and medical history of the subject, the dosing method and the like.

EXAMPLES

Hereinafter, the present invention will be illustrated in detail by examples, but is not limited thereto.

Example 1

Nucleic Acid Synthesis (1)

Ten kinds of nucleic acids shown in Table 2 were synthesized and supplied by GeneDesign, Inc. or the National Institute of Advanced Industrial Science and Technology in Tsukuba (AIST Tsukuba). Chemical synthesis of RNA chains was performed using tBDMS RNA amidites, chemical synthesis of DNA chains was performed using general DNA amidites, and S-modification (phosphorothioation) was performed using PADS. The synthesis method was based on a phosphoramidite method using a solid phase carrier (Scaringe, S. A. et al.; J. Am. Chem. 1998; 120: 11820-11821), and carried out using optimized parameters. The synthesizer used was an ns-8 nucleic acid synthesizer optimized for long-chain synthesis (manufactured by GeneDesign, Inc.). After completion of the synthesis, protecting groups present in base moieties and at position 2' were removed by a general method, and reverse-phase HPLC purification and subsequent desalination were performed to give a single strand. The thus-obtained two single strands were adjusted to appropriate concentrations, and mixed with a solution for double strand formation, which contains 4.1 mM Tris-HCl (pH 8.0) and 8.3 mM NaCl (final concentrations). After heating under an optimized temperature condition, gradual cooling to 30° C. with a temperature gradient of −1° C./min was performed to achieve double strand formation. After lyophilization, the desired nucleic acid was obtained. Nondenaturing gel electrophoresis on a 12% gel was performed, and double strand formation was confirmed from relative evaluation based on the migration positions of the single-stranded RNAs and a double-stranded marker. Regarding some of the 10 kinds of nucleic acids shown in Table 2, preparation of dsRNAs was performed using in vitro transcribed RNAs synthesized by use of a T7 transcription kit (EPICENTRE).

TABLE 2

| Nucleic acid (NA) | ssDNA[b] | Linker | dsRNA |
|---|---|---|---|
| NA1 | SEQ ID: 1 | SEQ ID: 9(DNA) complementary strand of SEQ ID: 9(RNA)[c] | SEQ ID: 5 complementary strand of SEQ ID: 5 |
| NA2 | SEQ ID: 1 | SEQ ID: 10(RNA) complementary strand of SEQ ID: 10(RNA) | SEQ ID: 5 complementary strand of SEQ ID: 5 |
| NA3[a] | SEQ ID: 1 | SEQ ID: 9(DNA) complementary strand of SEQ ID: 9(RNA)[c] | SEQ ID: 5 complementary strand of SEQ ID: 5 |
| NA4[a] | SEQ ID: 1 | SEQ ID: 9(DNA) complementary strand of SEQ ID: 9(RNA)[c] | SEQ ID: 6 complementary strand of SEQ ID: 6 |
| NA5[a] | SEQ ID: 2 | SEQ ID: 9(DNA) complementary strand of SEQ ID: 9(RNA)[c] | SEQ ID: 5 complementary strand of SEQ ID: 5 |
| NA6[a] | SEQ ID: 2 | SEQ ID: 9(DNA) complementary strand of SEQ ID: 9(RNA)[c] | SEQ ID: 7 complementary strand of SEQ ID: 7 |
| NA7[a] | SEQ ID: 3 | SEQ ID: 9(DNA) complementary strand of SEQ ID: 9(RNA)[c] | SEQ ID: 5 complementary strand of SEQ ID: 5 |
| NA8[a] | SEQ ID: 3 | SEQ ID: 9(DNA) complementary strand of SEQ ID: 9(RNA)[c] | SEQ ID: 7 complementary strand of SEQ ID: 7 |
| NA9[a] | SEQ ID: 4 | SEQ ID: 9(DNA) complementary strand of SEQ ID: 9(RNA)[c] | SEQ ID: 5 complementary strand of SEQ ID: 5 |
| NA10[a] | SEQ ID: 4 | SEQ ID: 9(DNA) complementary strand of SEQ ID: 9(RNA)[c] | SEQ ID: 7 complementary strand of SEQ ID: 7 |

[a]A nick is present between ssDNA/linker and dsRNA.
[b]Fully phosphorothioated
[c]The complementary base of A at position 1 of SEQ ID: 9 has been removed.

Example 2

Evaluation of IFN-β Promoter Activation

HEK293 cells ($2 \times 10^5$ cells/well) were seeded on 24-well culture plates. A human TLR3 expression vector (100 ng/well) together with a reporter plasmid p-125 (100 ng/well) and an internal control vector phRL-TK (5 ng/well, Promega) was transfected into HEK293 cells by use of FuGENE HD (Roche Diagnostics). The reporter plasmid p-125 contains a human IFN-β promoter (−125 to +19) and was kindly provided from Dr. Taniguchi, University of Tokyo. Control cells that were not allowed to express human TLR3 were also prepared. In either case, the total amount of DNA used for transfection was adjusted to 500 ng/well by addition of an empty vector. The culture medium used was Dulbecco's Modified Eagle's Medium-low glucose (Invitrogen) supplemented with 10% heat-inactivated fetal calf serum (FCS) and antibiotic(s).

After 24 hours from the transfection, the culture media were replaced by a culture medium without or with FCS, nucleic acids were added at a final concentration of 10 μg/mL each, and culture was performed for additional 6 hours. As the test nucleic acids, NA8 and NA10 shown in Table 2, FITC-labeled NA8, the endosomal localization sequence of NA8, the endosomal localization sequence of NA10, and the dsRNA portion common in NA8 and NA10 were used. As a positive control, poly IC was used. After the cells were washed and then lysed with a lysis buffer (Promega), firefly luciferase activity and renilla luciferase activity were quantified by use of a dual-luciferase reporter assay kit (Promega). The firefly luciferase activity was normalized to the renilla luciferase activity and represented as a relative strength of induction. This assay was performed in triplicate.

The results of the test performed using a culture medium without FCS are shown in FIG. 1. As is clear from FIG. 1, addition of NA8 or NA10 to TLR3-expressing cells showed a stronger induction than that of poly IC. FITC labeling did not affect the strength of induction. Meanwhile, addition of the NA8 endosomal localization sequence (NA8 ODN in the figure), the NA10 endosomal localization sequence (NA10 ODN in the figure), or the dsRNA portion (dsRNA in the figure) common in NA8 and NA10 showed no effects. These results clearly show that the nucleic acids of the present invention (NA8 and NA10) activate the IFN-β promoter via TLR3.

Figure 2:
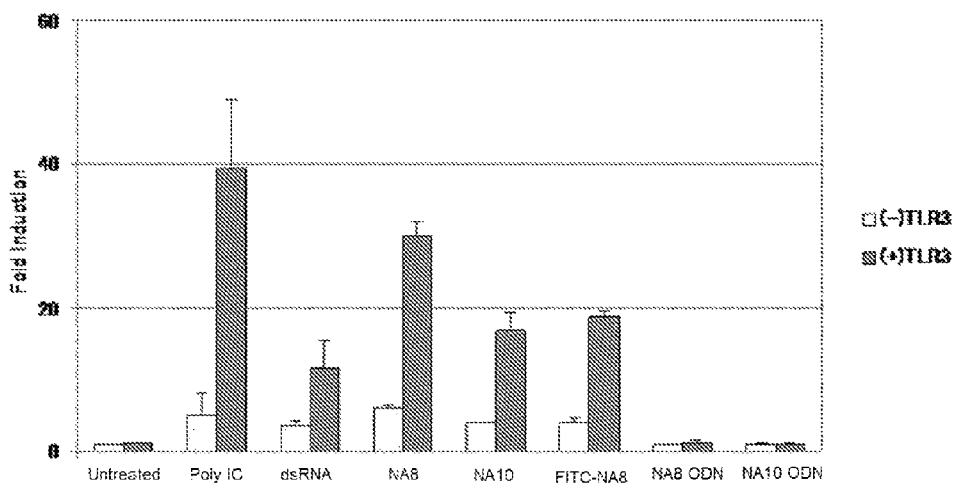
FIG. 2 shows the results of IFN-β promoter activation by nucleic acids of the present invention in a culture medium with FCS.
Figure 3:
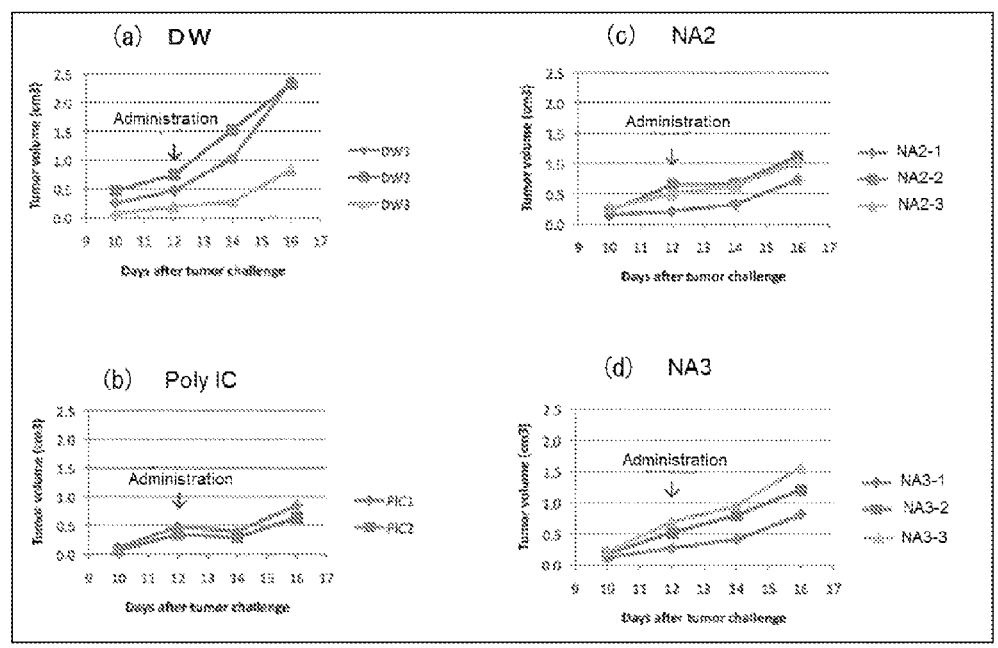
FIG. 3 shows the results of the 1st test for the effect on regression of transplanted cancer by nucleic acids of the present invention. (a) shows the results of a DW-administered group, (b) shows the results of a poly IC-administered group, (c) shows the results of an NA2-administered group, and (d) shows the results of an NA3-administered group.
Figure 4:
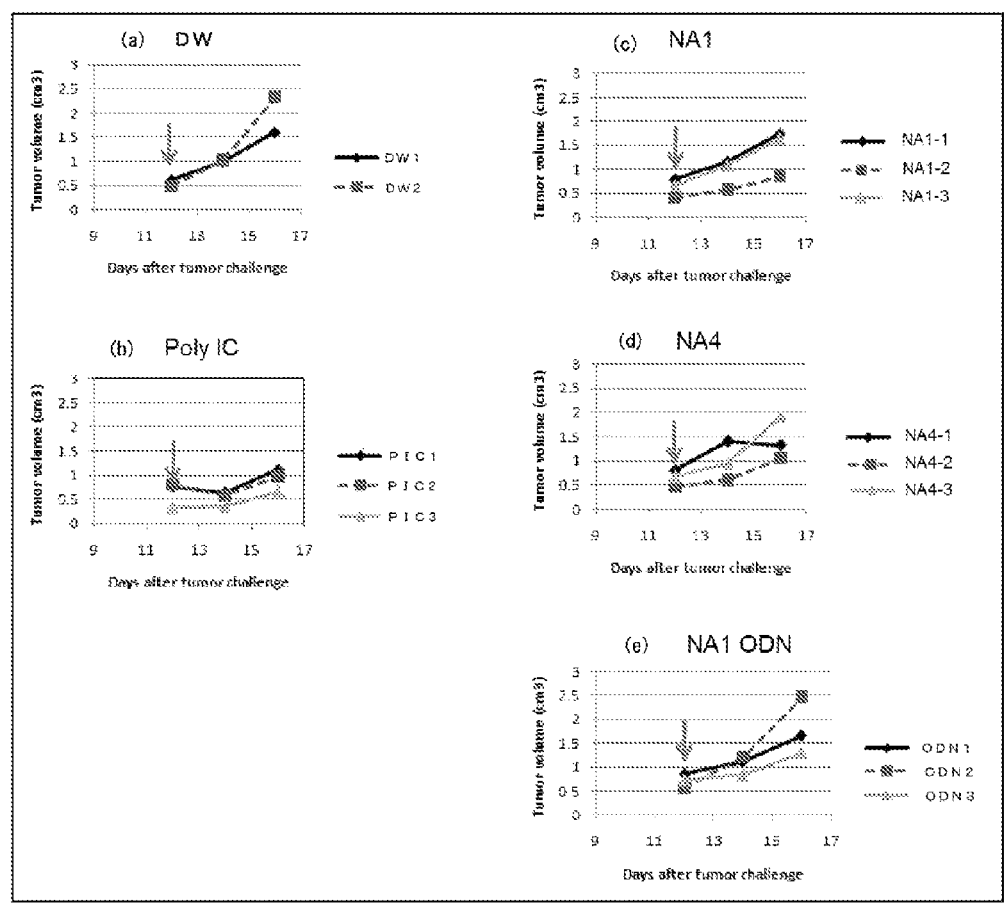
FIG. 4 shows the results of the 2nd test for the effect on regression of transplanted cancer by nucleic acids of the present invention. (a) shows the results of a DW-administered group, (b) shows the results of a poly IC-administered group, (c) shows the results of an NA1-administered group, (d) shows the results of an NA4-administered group, and (e) shows the results of an NA1 endosomal localization sequence (NA1 ODN)-administered group.

The results of the test performed using a culture medium with FCS are shown in FIG. 2. Although reduced activity had been expected due to the presence of RNase in FCS, NA8 and NA10 each activated the IFN-β promoter in TLR3-expressing cells as in the results shown in FIG. 1, albeit to a slightly lesser extent.

Example 3

Effect on Regression of Transplanted Cancer (1)

B16 melanoma cells (B16D8) were subcutaneously inoculated at $6 \times 10^5$ cells/200 μL/mouse to the flanks of C57BL/6J mice, and the tumor size (length×width$^2$×0.4) was measured over time. A test substance or a control substance was intraperitoneally administered at 12 days after the cell inoculation, and the tumor-regression effect was evaluated later. Since B16 melanoma cells do not express MHC class I molecules, the presence of the cells does not induce killer T cell activation. Therefore, if B16 melanoma tumors regress, this is attributed only to enhancement of NK cell activities through signaling mediated by TLR3 present in dendritic cells.

Two separate tests were performed. In the 1st test, NA2 and NA3 shown in Table 2 were used as test substances. In the 2nd test, NA1 and NA4 shown in Table 2, and the endosomal localization sequence of NA1 (which is the same as that of NA4) were used as test substances. In both tests, distilled water (DW) was administered to mice in a negative control group, and poly IC was administered to mice in a positive control group. The dose of each nucleic acid was 150 μg/mouse.

The results of the 1st test are shown in FIGS. 3(a) to (d). (a) shows the results of a DW-administered group (3 mice), (b) shows the results of a poly IC-administered group (2 mice), (c) shows the results of an NA2-administered group (3 mice), and (d) shows the results of an NA3-administered group (3 mice). As is clear from FIGS. 3(a) to (d), the nucleic acids of the present invention (NA2 and NA3) showed a tumor-regression effect comparable to that of poly IC.

The results of the 2nd test are shown in FIGS. 4(a) to (e). (a) shows the results of a DW-administered group (2 mice), (b) shows the results of a poly IC-administered group (3 mice), (c) shows the results of an NA1-administered group (3 mice), (d) shows the results of an NA4-administered group (3 mice), and (e) shows the results of an NA1 endosomal localization sequence (NA1 ODN)-administered group (3 mice). As is clear from FIGS. 4(a) to (e), the nucleic acids of the present invention (NA1 and NA4) showed a remarkable tumor-regression effect as compared with distilled water (DW), albeit to a lesser extent than poly IC. Meanwhile, administration of the NA1 endosomal localization sequence alone showed no tumor-regression effect, as shown in (e).

Example 4

Nucleic Acid Synthesis (2)

Twenty-one kinds of nucleic acids shown in Tables 3 and 4 were synthesized and supplied by GeneDesign, Inc. or AIST Tsukuba. The synthesis method was the same as that in Example 1.

TABLE 3

| Nucleic acid (NA) | ssDNA[b] | Linker | dsRNA |
|---|---|---|---|
| NA11[a] | SEQ ID: 3 | SEQ ID: 9(DNA) complementary strand of SEQ ID: 9(RNA)[c] | SEQ ID: 15 complementary strand of SEQ ID: 15 |
| NA12[a] | SEQ ID: 3 | SEQ ID: 9(DNA) complementary strand of SEQ ID: 9(RNA)[c] | SEQ ID: 17 complementary strand of SEQ ID: 17 |
| NA13[a] | SEQ ID: 3 | SEQ ID: 9(DNA) complementary strand of SEQ ID: 9(RNA)[c] | SEQ ID: 18 complementary strand of SEQ ID: 18 |
| NA14[a] | SEQ ID: 3 | SEQ ID: 9(DNA) complementary strand of SEQ ID: 9(RNA)[c] | SEQ ID: 19 complementary strand of SEQ ID: 19 |
| NA15[a] | SEQ ID: 3 | SEQ ID: 9(DNA) complementary strand of SEQ ID: 9(RNA)[c] | SEQ ID: 16 complementary strand of SEQ ID: 16 |
| NA16[a] | SEQ ID: 4 | SEQ ID: 9(DNA) complementary strand of SEQ ID: 9(RNA)[c] | SEQ ID: 16 complementary strand of SEQ ID: 16 |
| NA17[a] | SEQ ID: 1 | SEQ ID: 9(DNA) complementary strand of SEQ ID: 9(RNA)[c] | SEQ ID: 15 complementary strand of SEQ ID: 15 |
| NA18[a] | SEQ ID: 2 | SEQ ID: 9(DNA) complementary strand of SEQ ID: 9(RNA)[c] | SEQ ID: 15 complementary strand of SEQ ID: 15 |
| NA19[a] | SEQ ID: 2 | SEQ ID: 9(DNA) complementary strand of SEQ ID: 9(RNA)[c] | SEQ ID: 17 complementary strand of SEQ ID: 17 |
| NA20[a] | SEQ ID: 2 | SEQ ID: 9(DNA) complementary strand of SEQ ID: 9(RNA)[c] | SEQ ID: 18 complementary strand of SEQ ID: 18 |

[a]A nick is present between ssDNA/linker and dsRNA.
[b]Fully phosphorothioated
[c]The complementary base of A at position 1 of SEQ ID: 9 has been removed.

TABLE 4

| Nucleic acid (NA) | ssDNA[b] | Linker | dsRNA |
|---|---|---|---|
| NA21[a] | SEQ ID: 2 | SEQ ID: 9(DNA) complementary strand of SEQ ID: 9(RNA)[c] | SEQ ID: 19 complementary strand of SEQ ID: 19 |
| NA22[a] | SEQ ID: 2 | SEQ ID: 9(DNA) complementary strand of SEQ ID: 9(RNA)[c] | SEQ ID: 16 complementary strand of SEQ ID: 16 |
| NA23 | SEQ ID: 2 | SEQ ID: 10(RNA) complementary strand of SEQ ID: 10(RNA) | SEQ ID: 5 complementary strand of SEQ ID: 5 |
| NA24 | SEQ ID: 2 | N/A | SEQ ID: 5 complementary strand of SEQ ID: 5 |
| NA25 | SEQ ID: 2 | N/A | SEQ ID: 20 complementary strand of SEQ ID: 20 |
| NA26[a] | SEQ ID: 11 | SEQ ID: 9(DNA) complementary strand of SEQ ID: 9(RNA)[c] | SEQ ID: 16 complementary strand of SEQ ID: 16 |
| NA27[a] | SEQ ID: 14 | SEQ ID: 9(DNA) complementary strand of SEQ ID: 9(RNA)[c] | SEQ ID: 16 complementary strand of SEQ ID: 16 |
| NA28[a] | 5 bases from 5' end of SEQ ID: 2 | SEQ ID: 9(DNA) complementary strand of SEQ ID: 9(RNA)[c] | SEQ ID: 16 complementary strand of SEQ ID: 16 |
| NA29[a] | 10 bases from 5' end of SEQ ID: 2 | SEQ ID: 9(DNA) complementary strand of SEQ ID: 9(RNA)[c] | SEQ ID: 16 complementary strand of SEQ ID: 16 |
| NA30[a] | 15 bases from 5' end of SEQ ID: 2 | SEQ ID: 9(DNA) complementary strand of SEQ ID: 9(RNA)[c] | SEQ ID: 16 complementary strand of SEQ ID: 16 |
| NA31[a] | 20 bases from 5' end of SEQ ID: 2 | SEQ ID: 9(DNA) complementary strand of SEQ ID: 9(RNA)[c] | SEQ ID: 16 complementary strand of SEQ ID: 16 |

[a]A nick is present between ssDNA/linker and dsRNA.
[b]Fully phosphorothioated
[c]The complementary base of A at position 1 of SEQ ID: 9 has been removed.

Example 5

IFN-β Promoter Activation

The tests described below were performed with reporter plasmid p-125-transfected, human TLR3-expressing HEK293 cells and reporter plasmid p-125-transfected, human TLR3-non-expressing HEK293 cells (see Example 2).
(1) Examination of Effects of dsRNA Length on IFN-β Promoter Activating Capacity In the same manner as in Example 2, after 24 hours from transfection of various vectors, the culture media were replaced by a culture medium without FCS, test nucleic acids were added at a final concentration of 10 µg/mL each, and culture was performed for additional 6 hours. After the cells were washed and then lysed with a lysis buffer (Promega), luciferase activity was quantified by use of a dual-luciferase reporter assay kit (Promega) in the same manner as in Example 2. As the test nucleic acids, NA11 (dsRNA: 79 bps), NA12 (dsRNA: 99 bps), NA13 (dsRNA: 110 bps), NA14 (dsRNA: 119 bps), NA19 (dsRNA: 99 bps), NA20 (dsRNA: 110 bps), NA21 (dsRNA: 119 bps) and NA22 (dsRNA: 139 bps), all of which are shown in Tables 3 and 4, were used. As a positive control, poly IC was used.

Figure 5:
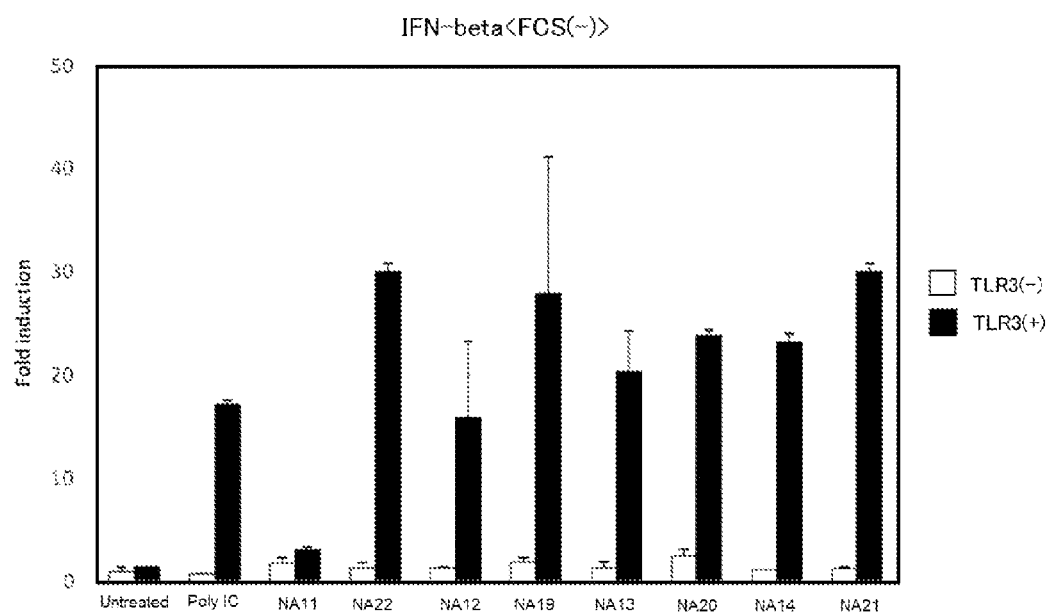
FIG. 5 shows the results of the effect that the length of dsRNA in the nucleic acid of the present invention makes on IFN-β promoter activation.

The results are shown in FIG. 5. As is clear from FIG. 5, in vitro TLR3-dependent activation of the IFN-β promoter requires a dsRNA having about 90 bps or more in length.

(2) Examination of Effects of Base Sequence of Endosomal Localization Sequence on IFN-β Promoter Activating Capacity In the same manner as in Example 2, after 24 hours from transfection of various vectors, the culture media were replaced by a culture medium without or with FCS, test nucleic acids were added at a final concentration of 10 µg/mL each, and culture was performed for additional 6 hours. After the cells were washed and then lysed with a lysis buffer (Promega), luciferase activity was quantified by use of a dual-luciferase reporter assay kit (Promega) in the same manner as in Example 2. As the test nucleic acids, NA16 (base sequence of ssDNA: SEQ ID NO: 4), NA22 (base sequence of ssDNA: SEQ ID NO: 2), NA26 (base sequence of ssDNA: SEQ ID NO: 11) and NA27 (base sequence of ssDNA: SEQ ID NO: 14), all of which are shown in Tables 3 and 4, were used. As a positive control, poly IC was used. In addition, endosomal localization sequences (ssDNA of SEQ ID NO: 4 (DNA4 in the figure), ssDNA of SEQ ID NO: 11 (DNA11 in the figure), and ssDNA of SEQ ID NO: 14 (DNA14 in the figure)) were separately used alone.

The results are shown in FIGS. 6(A) and (B). (A) shows the results of the test performed using a culture medium with FCS, and (B) shows the results of the test performed using a culture medium without FCS. In both culture media, NA26 containing an ssDNA (SEQ ID NO: 11) which is the same as that of SEQ ID NO: 2 except for having TpC instead of GpC, and NA27 containing an ssDNA (SEQ ID NO: 14) which is the same as that of SEQ ID NO: 4 except for having CpC instead of GpC were shown to have the TLR3-dependent IFN-β promoter activating capacity. Meanwhile, none of the endosomal localization sequences (ssDNAs) alone activated the IFN-β promoter.

(3) Examination of Effects of Endosomal Localization Sequence Length on IFN-β Promoter Activating Capacity In the same manner as in Example 2, after 24 hours from transfection of various vectors, the culture media were replaced by a culture medium without FCS, test nucleic acids were added at a final concentration of 10 µg/mL each, and culture was performed for additional 6 hours. After the cells were washed and then lysed with a lysis buffer (Promega), luciferase activity was quantified by use of a dual-luciferase reporter assay kit (Promega) in the same manner as in Example 2. As the test nucleic acids, NA28 (ssDNA length: 5 bases), NA29 (ssDNA length: 10 bases), NA30 (ssDNA length: 15 bases), NA31 (ssDNA length: 20 bases) and NA22 (ssDNA length: 25 bases), all of which are shown in Table 4, were used. As a positive control, poly IC was used.

Figure 7:
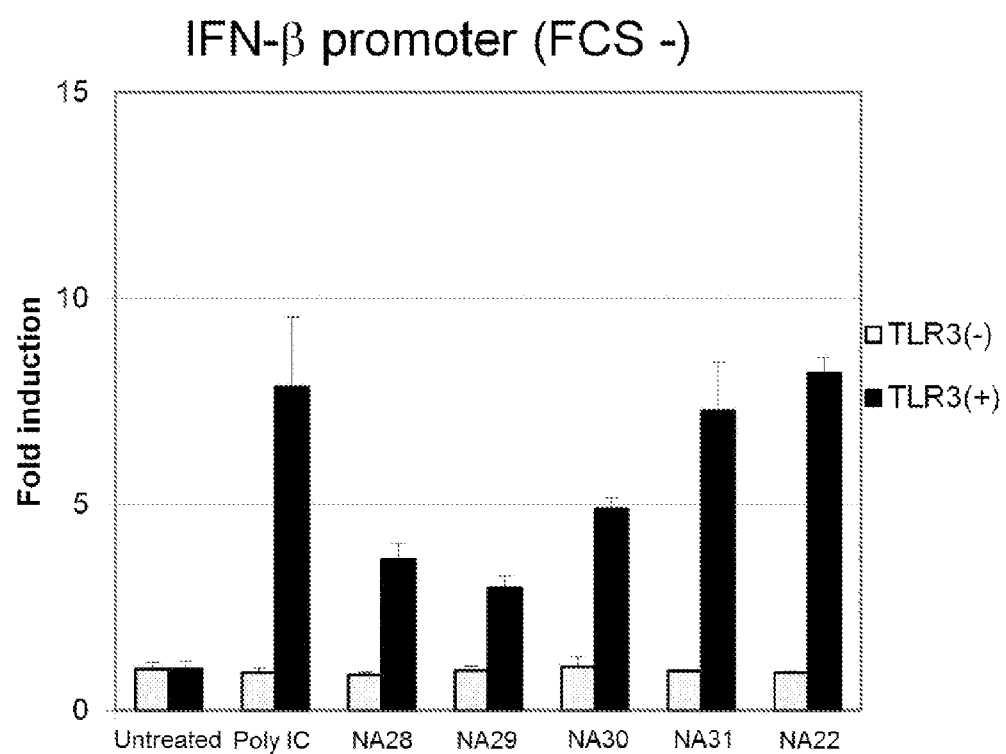
FIG. 7 shows the results of the effect that the length of the endosomal localization sequence (ssDNA) in the nucleic acid of the present invention makes on IFN-β promoter activation in a culture medium without FCS.

The results are shown in FIG. 7. As is clear from FIG. 7, even if the length of the endosomal localization sequence (ssDNA) is only 5 bases, the nucleic acid of the present invention has the in vitro TLR3-dependent IFN-β promoter activating capacity, but the length of the endosomal localization sequence (ssDNA) is preferably 15 bases or more, and more preferably 20 bases or more.

(4) Examination of IFN-β Promoter Activating Capacity via RIG-I/MDA5 Pathway

Into reporter plasmid p-125-transfected, human TLR3-non-expressing HEK293 cells (24-well plates), test nucleic acids (1 µg/well each) were individually transfected by use of Lipofectamine (Invitrogen), and culture was performed in a culture medium with FCS for 24 hours. After the cells were washed and then lysed with a lysis buffer (Promega), luciferase activity was quantified by use of a dual-luciferase reporter assay kit (Promega) in the same manner as in Example 2. Two separate tests were performed. In the 1st test, NA1, NA2, NA3, NA7, NA11, NA15, NA16 and NA17, all of which are shown in Tables 2 and 3, the ssDNA of SEQ ID NO: 3 (DNA3 in the figure), a dsRNA consisting of SEQ ID NO: 5 and its complementary strand (dsRNA5 in the figure), and a dsRNA consisting of SEQ ID NO: 16 and its complementary strand (dsRNA16 in the figure) were used as the test nucleic acids. As a positive control, poly IC was used. In the 2nd test, NA28 (ssDNA length: 5 bases), NA29 (ssDNA length: 10 bases), NA30 (ssDNA length: 15 bases), NA31 (ssDNA length: 20 bases) and NA22 (ssDNA length: 25 bases), all of which are shown in Table 4, and a dsRNA consisting of SEQ ID NO: 16 and its complementary strand (dsRNA16 in the figure) were used as the test nucleic acids. As a positive control, poly IC was used.

The results are shown in FIGS. 8(A) and (B). (A) shows the results of the 1st test and (B) shows the results of the 2nd test. As is clear from FIGS. 8(A) and (B), any of the simple dsRNAs activated RIG-I/MDA5 pathway, but none of the dsRNAs linked to an endosomal localization sequence (ssDNA) of 5 bases or more activated RIG-I/MDA5 pathway.

Example 6

TICAM-1-Dependent Cytokine Production (1) Cytokine Production in Dendritic Cells Isolated from Spleen (Splenic DCs)

The spleen was isolated from a C57BL/6J mouse (wild type: WT) or a TICAM-1 knockout mouse (TICAM-1 KO, created by the inventors) and then treated with collagenase. After filtration and hemolysis, washing was performed with a culture medium and CD11c positive cells were isolated by MACS system (miltenyi biotech) using anti-CD11c microbeads. The thus-obtained cells were used as splenic DCs.

The splenic DCs were seeded to a 24-well plate at $5 \times 10^5$ cells/500 µL culture medium/well, test nucleic acids (50 µg/mL each) were added, and culture was performed for 24 hours. As a culture medium, RPMI1640 containing 10% FCS, antibiotic(s), 10 mM HEPES and 55 µM 2-ME was used. After 24 hours, the culture supernatants were collected and the amounts of produced IL-6, TNF-α and IFN-β were measured by use of a BD CBA kit. As the test nucleic acids, NA23 and NA25 shown in Table 4 were used. As a positive control, poly IC was used.

The results are shown in FIGS. 9(A), (B) and (C). (A) shows the results of IL-6, (B) shows the results of TNF-α, and (C) shows the results of IFN-β. While wild-type mouse splenic DCs treated with NA23 or NA25 produced the three kinds of cytokines, TICAM-1 KO mouse splenic DCs treated with NA23 or NA25 hardly produced any of the cytokines.

These results show that the nucleic acid of the present invention exerts effect via TICAM-1-mediated signal transduction.

(2) Cytokine Production in Dendritic Cells Isolated from Bone Marrow (BMDCs)

A bone marrow aspirate was obtained from the femur of a C57BL/6J mouse (wild type: WT) or a TICAM-1 knockout mouse (TICAM-1 KO). After hemolysis, the aspirate was suspended in a culture medium (RPMI 1640/10% FCS/2-ME/HEPES) supplemented with recombinant murine GM-CSF (final 10 ng/mL, Peprotech). The suspension was seeded to a 24-well plate at $1 \times 10^6$ cells/mL/well, and culture was performed at 37° C. The culture media were replaced by a fresh culture medium containing rmGM-CSF (10 ng/mL) at intervals of two days, and non-adherent cells were collected on the 6th day. The thus-obtained cells were used as BMDCs.

The BMDCs were seeded to a 96-well round-bottom plate at $1 \times 10^5$ cells/200 µL serum-free AIM medium (GIBCO)/well, test nucleic acids (10 µg/mL each) were added, and culture was performed for 24 hours. After 24 hours, the culture supernatants were collected and the amounts of produced IL-6 and TNF-α were measured by use of a BD CBA kit. As the test nucleic acids, NA1 and NA2 shown in Table 2 were used. As a positive control, poly IC was used.

The results are shown in FIGS. 10(A) and (B). (A) shows the results of IL-6 and (B) shows the results of TNF-α. TICAM-1 KO mouse BMDCs showed a remarkably reduced cytokine production as compared with wild-type mouse BMDCs. These results show that the nucleic acid of the present invention exerts effect via TICAM-1-mediated signal transduction.

Example 7

NK Activity Enhancing Effect

The spleen was isolated from a C57BL/6J mouse, mashed through a mesh and collected into a 15-mL tube. After hemolysis, washing was performed with a culture medium and DX5-positive NK cells were isolated by MACS system (miltenyi biotech) using anti-CD49b (DX5) microbeads.

The BMDCs isolated in Example 6 (2) (cells on the 6th day after isolation) were seeded on a 96-well round-bottom plate at $1 \times 10^5$ cells/200 µL serum-free AIM medium (GIBCO)/well, and test nucleic acids (10 µg/mL each) were added for pre-stimulation. After 4 hours of pre-stimulation, the isolated NK cells (DX5-positive cells) were added at $2 \times 10^5$ cells/well, and co-cultured with the BMDCs at 37° C. for 24 hours. After 24 hours, the culture supernatants were collected and the amount of produced IFN-γ was measured by ELISA (eBioscience).

The results are shown in Table 5. These results show that the nucleic acid of the present invention is delivered to endosomes of BMDCs and activates TLR3, and thereby induces NK cell activation and an increased production of IFN-γ.

TABLE 5

| Nucleic acid (NA) | IFN-γ (pg) |
|---|---|
| NA1 | 1150 |
| NA2 | 3000 |
| NA3 | 795 |
| NA17 | 1300 |
| NA19 | 980 |
| NA20 | 930 |
| NA21 | 765 |
| NA22 | 520 |
| Poly IC | 1250 |

TABLE 5-continued

| Nucleic acid (NA) | IFN-γ (pg) |
|---|---|
| dsRNA-1* | 660 |
| dsRNA-2** | 314 |

*SEQ ID: 16 and its complementary strand
**SEQ ID: 5 and its complementary strand Example 8

In Vivo Cytokine Production

Test nucleic acids (50 µg each) were intraperitoneally administered to C57BL/6J mice (8- to 12-week old, female). The blood samples were collected under anesthesia at 1, 3 and 6 hours from the administration, and the amounts of TNF-α, IL-6 and IL-10 in sera were measured by use of a BD CBA kit. As the test nucleic acids, NA2 shown in Table 2, and NA22 and NA23 shown in Table 4 were used. As a control nucleic acid, an endosomal localization sequence (ssDNA of SEQ ID NO: 1 (DNA1 in the figure)) was used alone. As a positive control, poly IC (200 µg) was used.

The results are shown in FIGS. 11(A) to (E). (A) shows the results of TNF-α for NA2, (B) shows the results of IL-6 for NA2, (C) shows the results of TNF-α for NA22 and NA23, (D) shows the results of IL-6 for NA22 and NA23, and (E) shows the results of IL-10 for NA22 and NA23. The nucleic acids of the present invention showed a remarkable reduction in in vivo cytokine production as compared with the positive control poly IC. These results indicate that the nucleic acid of the present invention administered to a living body has no risk of side effects such as cytokine storm and is highly safe.

Example 9

Effect on Regression of Transplanted Cancer (2)

(1) Effect on B16 Melanoma-Bearing Wild-Type Mice

B16 melanoma cells (B16D8) were subcutaneously inoculated at $6 \times 10^5$ cells/200 µL/mouse to the flanks of C57BL/6J mice, and the tumor size (length×width$^2$×0.4) was measured over time. A test substance or a control substance was intraperitoneally administered at 12 days after the cell inoculation, and the tumor-regression effect was evaluated later. As the test substance, NA22 shown in Table 4 was used. Distilled water (DW) was administered to mice in a negative control group, and poly IC was administered to mice in a positive control group. The dose of each nucleic acid was 150 µg/mouse. Since B16 melanoma cells do not express MHC class I molecules, the presence of the cells does not induce killer T cell activation. Therefore, if B16 melanoma tumors regress, this is attributed only to enhancement of NK cell activities through signaling mediated by TLR3 present in dendritic cells.

The results are shown in FIG. 12. As is clear from FIG. 12, NA22 showed a tumor-regression effect comparable to that of poly IC.

(2) Effect on EL4-Bearing Wild-Type Mice

EL4 cells (mouse lymphoma cells) were subcutaneously inoculated at $1 \times 10^6$ cells/200 µL/mouse to the flanks of C57BL/6J mice, and the tumor size (length×width$^2$×0.4) was measured over time. A test substance or a control substance was intraperitoneally administered at 7 and 11 days after the cell inoculation, and the tumor-regression effect was evaluated later. As the test substance, NA24 or NA25 shown in Table 4 was used. Distilled water (DW) was administered to mice in a negative control group, and poly IC was administered to mice in a positive control group. The dose of each nucleic acid was 200 μg/mouse. The EL4-bearing mouse is a model for evaluation of CTL-dependent antitumor effect.

The results are shown in FIG. 13. As is clear from FIG. 13, NA24 and NA25 each showed a remarkable tumor-regression effect as compared with distilled water (DW), albeit to a lesser extent than poly IC.

(3) Effect on B16 Melanoma-Bearing TICAM-1 KO Mice

B16 melanoma cells (B16D8) were subcutaneously inoculated at $6 \times 10^5$ cells/200 μL/mouse to the flanks of C57BL/6J mice (wild-type: WT) and TICAM-1 knockout mice (TICAM-1 KO), and the tumor size (length×width$^2$×0.4) was measured over time. A test substance or a control substance was intraperitoneally administered at 11 days after the cell inoculation, and the tumor-regression effect was evaluated later. As the test substance, NA25 shown in Table 4 was used. As a control substance, distilled water (DW) was administered. The dose of the nucleic acid was 250 μg/mouse.

Figure 14:
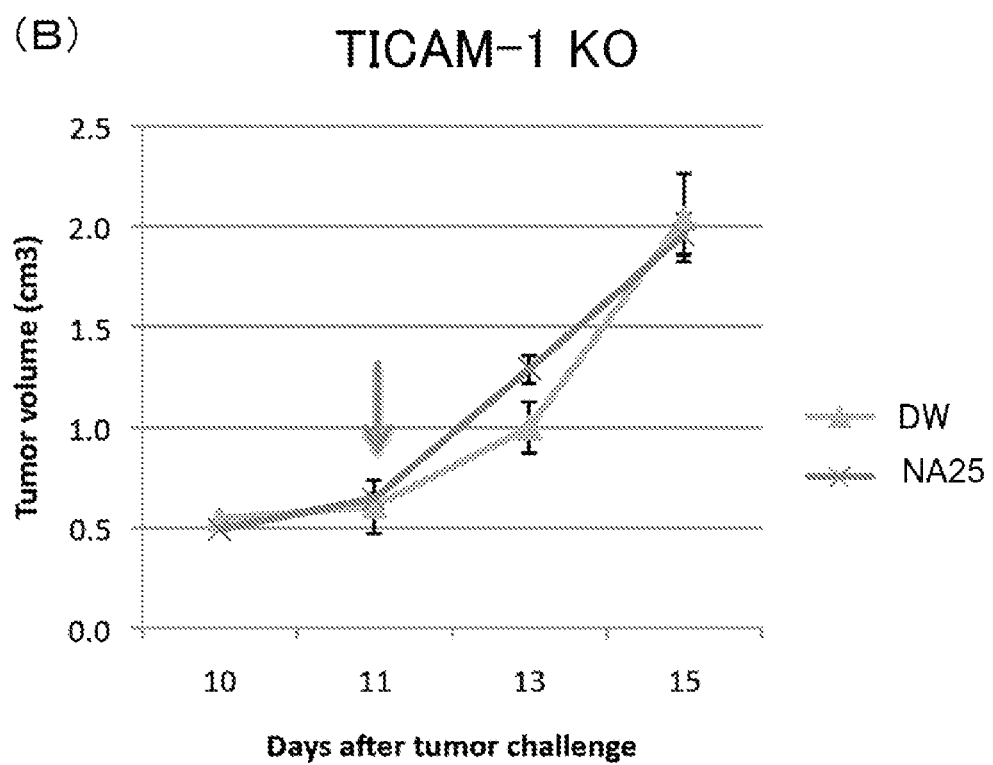
FIG. 14(A) shows the results of the effect on regression of transplanted cancer by a nucleic acid of the present invention in B16 melanoma-bearing wild-type mice.
FIG. 14(B) shows the results of the effect on regression of transplanted cancer by a nucleic acid of the present invention in B16 melanoma-bearing TICAM-1 KO mice.

The results are shown in FIGS. 14(A) and (B). (A) shows the results for the wild-type mice and (B) shows the results for the TICAM-1 KO mice. NA25 showed a remarkable tumor-regression effect as compared with distilled water (DW) in the wild-type mice, but did not show tumor-regression effect in the TICAM-1 KO mice. These results show that the nucleic acid of the present invention exerts effect via TICAM-1-mediated signal transduction.

(4) Effect on Regression of Transplanted Cancer by Nucleic Acid Administration Using In Vivo jetPEI In vivo jetPEI (Funakoshi Co., Ltd.) is a transfection reagent for in vivo experiments. By use of this reagent, the nucleic acid of the present invention was subcutaneously administered in the vicinity of a tumor, and the effect on regression of transplanted cancer was evaluated later.

B16 melanoma cells (B16D8) were subcutaneously inoculated at $6 \times 10^5$ cells/200 μL/mouse to the flanks of C57BL/6J mice, and the tumor size (length×width$^2$×0.4) was measured over time. A test substance or a control substance was subcutaneously administered at 12 days after the cell inoculation, and the tumor-regression effect was evaluated later. As the test substance, NA25 shown in Table 4 was used. Distilled water (DW) was administered to mice in a negative control group, and poly IC was administered to mice in a positive control group. The dose of each nucleic acid was 50 μg/mouse. The solution for nucleic acid administration was prepared as follows. Solution A (10% glucose: 50 μL, nucleic acid (50 μg), and DW (DNase- and RNase-free, Ambion): quantity sufficient to 100 μL), and solution B (10% glucose: 50 μL, DW (DNase- and RNase-free, Ambion): 43 μL, and in vivo jetPEI: 7 μL) were separately prepared. Solution A and solution B were mixed and gently stirred, and then incubated at room temperature for 15 minutes. The resulting nucleic acid solution was administered subcutaneously into two sites in the vicinity of a tumor in a volume of 100 μL per site.

Figure 15:
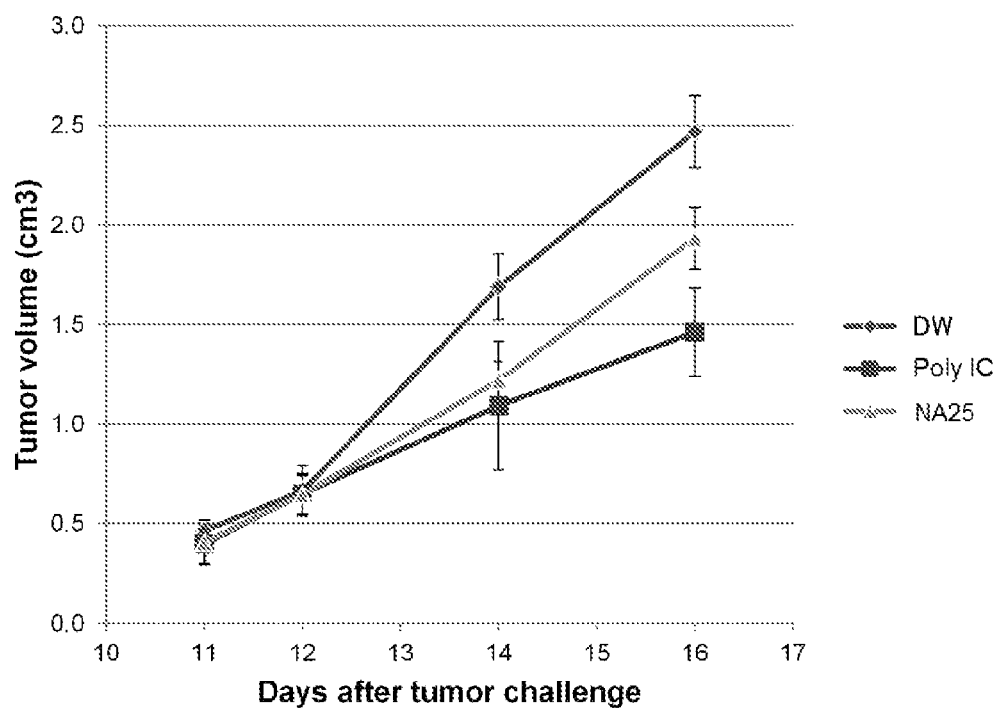
FIG. 15 shows the results of the effect on regression of transplanted cancer by a nucleic acid of the present invention in B16 melanoma-bearing wild-type mice that have subjected to subcutaneous administration of the nucleic acid with an in vivo transfection reagent into the vicinity of a tumor.

The results are shown in FIG. 15. As is clear from FIG. 15, NA25 showed a remarkable tumor-regression effect as compared with distilled water (DW), albeit to a lesser extent than poly IC.

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literatures cited in the above description are incorporated herein by reference.

The invention claimed is:

1. A nucleic acid at least containing a single-stranded DNA to be delivered to endosomes of dendritic cells and a double-stranded RNA capable of activating TLR3 wherein the double-stranded RNA capable of activating TLR3 is an RNA consisting of the base sequence of any one of the group consisting of SEQ ID NOS: 5 to 7 and 15 to 20, and of a complementary sequence thereof.

2. The nucleic acid according to claim 1, wherein the single-stranded DNA is any of the following (a) to (d):
   (a) a type-B or -C CpG-DNA having TLR9 ligand activity,
   (b) a DNA which is the same as the above (a) except that GpC is substituted for each instance of CpG,
   (c) a DNA which is the same as the above (b) except that TpC is substituted for each instance of GpC, and
   (d) a DNA which is the same as the above (b) except that CpC is substituted for each instance of GpC.

3. The nucleic acid according to claim 2, wherein the single-stranded DNA consists of a base sequence shown in any of SEQ ID NOS: 1 to 4 and 11 to 14, or of a partial sequence thereof.

4. The nucleic acid according to claim 1, wherein the single-stranded DNA is 15 bases or more in length.

5. The nucleic acid according to claim 1, wherein all or part of nucleotides which constitute the single-stranded DNA are phosphorothioated.

6. The nucleic acid according to claim 1, wherein the single-stranded DNA is linked to the double-stranded RNA via a linker sequence.

7. The nucleic acid according to claim 1, wherein the single-stranded DNA is directly linked to the double-stranded RNA.

8. A pharmaceutical composition containing the nucleic acid according to claim 1.

9. An IFN-β expression enhancer containing the nucleic acid according to claim 1 as an active ingredient.

10. An NK cell activator containing the nucleic acid according to claim 1 as an active ingredient.

11. A cytotoxic T cell inducer containing the nucleic acid according to claim 1 as an active ingredient.

12. An immunostimulant containing the nucleic acid according to claim 1 as an active ingredient.

13. A vaccine adjuvant containing the nucleic acid according to claim 1 as an active ingredient.

14. A cancer therapeutic agent containing the nucleic acid according to claim 1 as an active ingredient.

* * * * *

SEQUENCE LISTING

<160> NUMBER OF SEQ ID NOS: 20

<210> SEQ ID NO 1
<211> LENGTH: 25
<212> TYPE: DNA
<213> ORGANISM: Artificial
<220> FEATURE:
<223> OTHER INFORMATION: synthetic DNA

<400> SEQUENCE: 1
tcgtcgtcgt tcgaacgacg ttgat                                    25

<210> SEQ ID NO 2
<211> LENGTH: 25
<212> TYPE: DNA
<213> ORGANISM: Artificial
<220> FEATURE:
<223> OTHER INFORMATION: synthetic DNA

<400> SEQUENCE: 2
tgctgctgct tgcaagcagc ttgat                                    25

<210> SEQ ID NO 3
<211> LENGTH: 24
<212> TYPE: DNA
<213> ORGANISM: Artificial
<220> FEATURE:
<223> OTHER INFORMATION: synthetic DNA

<400> SEQUENCE: 3
tcgtcgtttt gtcgttttgt cgtt                                          24

<210> SEQ ID NO 4
<211> LENGTH: 24
<212> TYPE: DNA
<213> ORGANISM: Artificial
<220> FEATURE:
<223> OTHER INFORMATION: synthetic DNA

<400> SEQUENCE: 4
tgctgctttt gtgcttttgt gctt                                          24

<210> SEQ ID NO 5
<211> LENGTH: 58
<212> TYPE: RNA
<213> ORGANISM: Measles virus strain Edmonston

<400> SEQUENCE: 5
ggauacagug cccugauuaa ggacuaauug guugaacucc ggaacccuaa uccugccc     58

<210> SEQ ID NO 6
<211> LENGTH: 79
<212> TYPE: RNA
<213> ORGANISM: Measles virus strain Edmonston

<400> SEQUENCE: 6
cccggugguu aggcauuauu ugcaauauau uaagaaaac uuugaaaaua cgaaguuucu     60
auucccagcu uugucuggu                                                 79

<210> SEQ ID NO 7
<211> LENGTH: 139
<212> TYPE: RNA
<213> ORGANISM: Measles virus strain Edmonston

<400> SEQUENCE: 7
cccggauaca gucccugau uaaggacuaa uugguugaac uccggaaccc uaauccugcc     60
cuaggugguu aggcauuauu ugcaauauau uaagaaaac uuugaaaaua cgaaguuucu    120
auucccagcu uugucuggu                                                139

<210> SEQ ID NO 8
<211> LENGTH: 1152
<212> TYPE: RNA
<213> ORGANISM: Measles virus strain Edmonston

<400> SEQUENCE: 8
accagacaaa gcugggaaua gaaacuucgu auuucaaag uuucuuuaa uauauugcaa      60 auaaugccua accaccuagg gcaggauuag gguuccggag uucaaccaau uaguccuuaa    120
ucagggcacu guauccgacu aacuuauacc auucuuuggu cuccuugacu guuaccuuaa    180
aaacccacuc acguuucaaa cccccguca uaauaaucug uuucucgac uuggauagau     240 ucuuaacgaa gauauucugg guaagucuua guacagauua gccggacuug agauucugga    300
uaaacuuauu uaucaacuuu cuguucccgg aguaaagaag aaugugcccc caaauuugc    360 gggugauccu agauauaagu ucucguugcc ugcacuuac caauacgggg uaagcgugga    420
acaucccuug uugacuucuu ugguugucuu ugaaucuugc caacuccccug uagaggauga    480 guauagaauu aagcaauccc ucuugcccug aggcaacauc augggggauc aauucuuugc    540
acagcuuagg uccguuaauu gccaacccgc aauugaucag caccucgcucu auaggguguaa    600 guuuuuucag aguaggauug auaucaccuc uacuaacugc gucucccaca auugcuugua    660

```
ugcagcuuag uugcuuaaug gauaggaugu gaccuauaag uccaggugaa guccucacag    720
augauucaau uaucugcugc uuaaucuuuu caggauucau uagccgguua gccuugagau    780
cugucauaac caaauaagau ucaguagaua ugaaguugcu guaucuaggg uauacaaggu    840
ucacuucucu auaugagac ccuacauaac uuauaaaucc cugaacaaaa uccccgcuga     900
aaggcauaag cuuaaucacc aguauugauc cuauuuugcc caggagcaga gccaucgaua    960
agauggcugc caauuccucu agcuucucua uaguaucuuu guuaggcaag uuagucggau   1020
acagugcccu gauuaaggac uaauugguug aacuccggaa cccuaauccu gcccuaggug   1080
guuaggcauu auuugcaaua uauuaagaa  aacuuugaaa auacgaaguu ucuauuccca   1140
gcuuugucug gu                                                       1152
```

```
<210> SEQ ID NO 9
<211> LENGTH: 16
<212> TYPE: DNA
<213> ORGANISM: Artificial
<220> FEATURE:
<223> OTHER INFORMATION: synthetic DNA

<400> SEQUENCE: 9
accgtggtca tgctcc                                                     16

<210> SEQ ID NO 10
<211> LENGTH: 16
<212> TYPE: RNA
<213> ORGANISM: Artificial
<220> FEATURE:
<223> OTHER INFORMATION: synthetic RNA

<400> SEQUENCE: 10
accgugguca ugcucc                                                     16

<210> SEQ ID NO 11
<211> LENGTH: 25
<212> TYPE: DNA
<213> ORGANISM: Artificial
<220> FEATURE:
<223> OTHER INFORMATION: synthetic DNA

<400> SEQUENCE: 11
ttcttcttct ttcaatcatc ttgat                                           25

<210> SEQ ID NO 12
<211> LENGTH: 25
<212> TYPE: DNA
<213> ORGANISM: Artificial
<220> FEATURE:
<223> OTHER INFORMATION: synthetic DNA

<400> SEQUENCE: 12
tcctcctcct tccaaccacc ttgat                                           25

<210> SEQ ID NO 13
<211> LENGTH: 24
<212> TYPE: DNA
<213> ORGANISM: Artificial
<220> FEATURE:
<223> OTHER INFORMATION: synthetic DNA

<400> SEQUENCE: 13 ttcttcttttt gttcttttgt tctt                                           24
```

```
<210> SEQ ID NO 14
<211> LENGTH: 24
<212> TYPE: DNA
<213> ORGANISM: Artificial
<220> FEATURE:
<223> OTHER INFORMATION: synthetic DNA

<400> SEQUENCE: 14
tcctcctttt gtcctttgt cctt                                             24

<210> SEQ ID NO 15
<211> LENGTH: 79
<212> TYPE: RNA
<213> ORGANISM: Measles virus strain Edmonston

<400> SEQUENCE: 15
ggugguuagg cauuauuugc aauauauuaa agaaaacuuu gaaaauacga aguuucuauu      60
cccagcuuug ucgguccc                                                    79

<210> SEQ ID NO 16
<211> LENGTH: 139
<212> TYPE: RNA
<213> ORGANISM: Measles virus strain Edmonston

<400> SEQUENCE: 16 ggaucagug cccugauuaa ggacuaauug guugaacucc ggaacccuaa uccugcccua       60 gguguuagg cauuauuugc aauauauuaa agaaaacuuu gaaaauacga aguuucuauu      120
cccagcuuug ucgguccc                                                  139

<210> SEQ ID NO 17
<211> LENGTH: 99
<212> TYPE: RNA
<213> ORGANISM: Measles virus strain Edmonston

<400> SEQUENCE: 17
ggaacccuaa uccugcccua gguguuagg cauuauuugc aauauauuaa agaaaacuuu       60
gaaaauacga aguuucuauu cccagcuuug ucgguccc                              99

<210> SEQ ID NO 18
<211> LENGTH: 110
<212> TYPE: RNA
<213> ORGANISM: Measles virus strain Edmonston

<400> SEQUENCE: 18
gguugaacuc cggaacccua uccugcccu aggugguuag gcauuauuug caauauauua       60 agaaaacuu ugaaaauacg aaguuucuau ucccagcuuu gucgguccc                  110

<210> SEQ ID NO 19
<211> LENGTH: 119
<212> TYPE: RNA
<213> ORGANISM: Measles virus strain Edmonston

<400> SEQUENCE: 19
ggacuaauug guugaacucc ggaacccuaa uccugcccua gguguuagg cauuauuugc       60 aauauauuaa agaaaacuuu gaaaauacga aguuucuauu cccagcuuug ucgguccc      119

<210> SEQ ID NO 20
<211> LENGTH: 73
<212> TYPE: RNA
<213> ORGANISM: Measles virus strain Edmonston
```

```
<400> SEQUENCE: 20
ggauacagug cccugauuaa ggacuaauug guugaacucc ggaacccuaa uccugcccua       60
ggugguuagg cau                                                         73
```